US008377952B2

(12) United States Patent
Rosenberg et al.

(10) Patent No.: US 8,377,952 B2
(45) Date of Patent: Feb. 19, 2013

(54) SOLID PHARMACEUTICAL DOSAGE FORMULATION

(75) Inventors: Jöerg Rosenberg, Ellerstadt (DE); Ulrich Reinhold, Aachen (DE); Bernd Liepold, Heidelberg (DE); Gunther Berndl, Herxheim (DE); Jörg Breitenbach, Mannheim (DE); Laman L. Alani, Lansdale, PA (US); Soumojeet Ghosh, Lansdale, PA (US)

(73) Assignee: Abbott Laboratories, Abbott Park, IL (US)

( * ) Notice: Subject to any disclaimer, the term of this patent is extended or adjusted under 35 U.S.C. 154(b) by 971 days.

(21) Appl. No.: 11/064,467

(22) Filed: Feb. 23, 2005

(65) Prior Publication Data

US 2005/0143404 A1 Jun. 30, 2005

(51) Int. Cl.
*A61K 31/513* (2006.01)
*A61K 31/427* (2006.01)
(52) U.S. Cl. .................... 514/269; 514/370
(58) Field of Classification Search ............ 514/269, 514/370
See application file for complete search history.

(56) References Cited

U.S. PATENT DOCUMENTS

| | | | |
|---|---|---|---|
| 4,540,602 A | 9/1985 | Motoyama et al. |
| 4,590,065 A | 5/1986 | Piechota, Jr. et al. |
| 4,758,427 A | 7/1988 | Leeson |
| 4,769,236 A | 9/1988 | Panoz et al. |
| 4,801,460 A | 1/1989 | Goertz et al. |
| 4,806,337 A | 2/1989 | Snipes et al. |
| 4,851,438 A | 7/1989 | Flashinski |
| 4,880,585 A | 11/1989 | Klimesch et al. |
| 4,904,699 A | 2/1990 | Bauer |
| 4,957,681 A | 9/1990 | Klimesch et al. |
| 4,996,058 A | 2/1991 | Sinnreich |
| 5,073,379 A | 12/1991 | Klimesch et al. |
| 5,145,683 A | 9/1992 | Rhodes |
| 5,368,864 A | 11/1994 | Lahr et al. |
| 5,403,923 A | 4/1995 | Kashimura et al. |
| 5,405,616 A | 4/1995 | Wunderlich et al. |
| 5,456,923 A | 10/1995 | Nakamichi et al. |
| 5,476,667 A | 12/1995 | Kristensen et al. |
| 5,484,926 A | 1/1996 | Dressman et al. |
| 5,490,990 A | 2/1996 | Grabowski et al. |
| 5,501,858 A | 3/1996 | Fuisz |
| 5,525,628 A | 6/1996 | Nicola et al. |
| 5,541,206 A | 7/1996 | Kempf et al. |
| 5,545,628 A | 8/1996 | Deboeck et al. |
| 5,552,159 A | 9/1996 | Mueller et al. |
| 5,559,158 A | 9/1996 | Al-Razzak et al. |
| 5,567,823 A | 10/1996 | Tien et al. |
| 5,585,397 A | 12/1996 | Tung et al. |
| 5,610,193 A | 3/1997 | Al-Razzak et al. |
| 5,635,523 A | 6/1997 | Kempf et al. |
| 5,641,516 A | 6/1997 | Grabowski et al. |
| 5,648,497 A | 7/1997 | Kempf et al. |
| 5,654,003 A | 8/1997 | Fuisz et al. |
| 5,674,882 A | 10/1997 | Kempf et al. |
| 5,695,784 A | 12/1997 | Pollinger et al. |
| 5,707,648 A | 1/1998 | Yiv |
| 5,725,878 A | 3/1998 | Al-Razzak et al. |
| 5,727,878 A | 3/1998 | Sullivan, Jr. |
| 5,741,519 A | 4/1998 | Rosenberg et al. |
| 5,762,961 A | 6/1998 | Roser et al. |
| 5,773,025 A | 6/1998 | Baichwal |
| 5,776,495 A | 7/1998 | Duclos et al. |
| 5,834,472 A | 11/1998 | Sangekar et al. |
| 5,852,195 A | 12/1998 | Romines et al. |
| 5,858,401 A | 1/1999 | Bhalani et al. |
| 5,889,051 A | 3/1999 | Chen et al. |
| 5,897,910 A | 4/1999 | Rosenberg et al. |
| 5,914,332 A | 6/1999 | Sham et al. |
| 5,935,936 A | 8/1999 | Fasbender et al. |
| 5,939,099 A | 8/1999 | Grabowski et al. |
| 5,945,123 A | 8/1999 | Hermelin |
| 5,945,127 A | 8/1999 | Breitenbach et al. |
| 5,948,426 A | 9/1999 | Jefferies |
| 5,948,436 A | 9/1999 | Al-Razzak et al. |
| 5,955,475 A | 9/1999 | Krape et al. |
| 5,958,452 A | 9/1999 | Oshlack et al. |
| 5,958,455 A | 9/1999 | Roser et al. |
| 5,965,161 A | 10/1999 | Oshlack et al. |
| 5,965,163 A | 10/1999 | Miller et al. |
| 5,969,181 A | 10/1999 | Breitenbach et al. |
| 6,001,391 A | 12/1999 | Zeidler et al. |
| 6,009,690 A | 1/2000 | Rosenberg et al. |
| 6,027,747 A | 2/2000 | Terracol et al. |

(Continued)

FOREIGN PATENT DOCUMENTS

| AU | 3113893 | 7/1993 |
|---|---|---|
| CA | 1270201 A1 | 6/1990 |

(Continued)

OTHER PUBLICATIONS

International Search Report & Written Opinion from PCT/US2006/005944 dated Aug. 4, 2006.
Aungst, B.J., et al., "Improvd Oral Bioavailability of an HIV Protease Inhibitor Using Gelucire 44/14 and Labrasol Vehicles", *B. T. Gattetosse*, 87:49-54 (1994).
Awni, W., et al., "Significantly Reduced Food Effect and Pharmacokinetic Variability with a Novel Lopinavir/ritonavir Tablet Formulation", *Third IAS Conf on HIV Pathogenesis and Treatment*, (2005).
Breitenbach, "Melt extrusion: from process to drug delivery technology", J., *Eur. J of Pharm. & Biopharm.*, 54:107-117(2002).
Forster, A., et al., "Selection of excipients for melt extrusion with two poorly water-soluble drugs by solubility parameter calculation and thermal analysis", *Int'l. J. of Pharmaceutics*, 226:147-161 (2001).

(Continued)

*Primary Examiner* — San-Ming Hui
*Assistant Examiner* — Kathrien Cruz
(74) *Attorney, Agent, or Firm* — Xu Zhang

(57) ABSTRACT

The present invention provides a pharmaceutical dosage formulation, and more particularly, to a pharmaceutical dosage formulation comprising an HIV protease inhibitor.

35 Claims, 2 Drawing Sheets

U.S. PATENT DOCUMENTS

Figure 1:
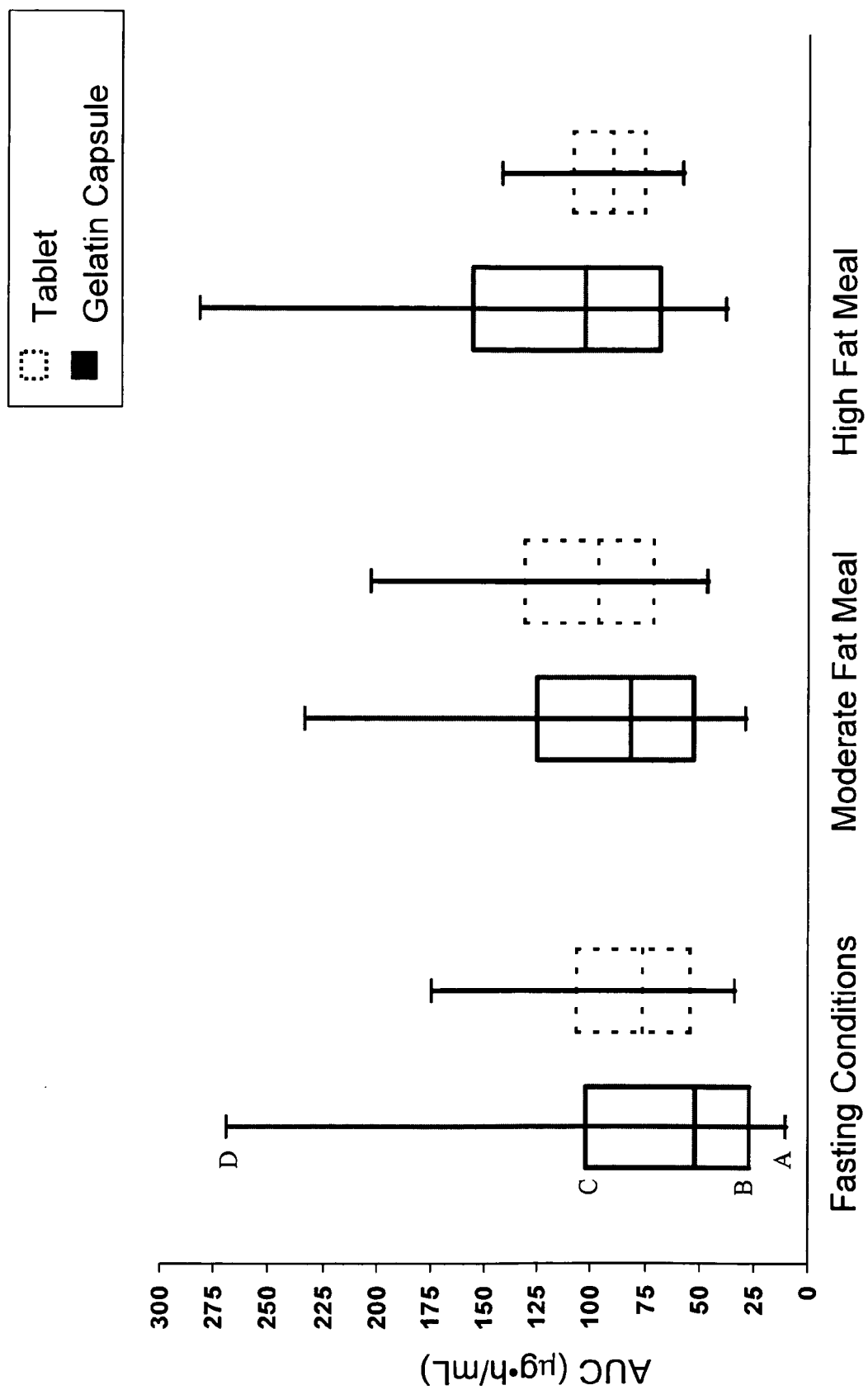

| | | | |
|---|---|---|---|
| 6,037,157 A | 3/2000 | Norbeck et al. | |
| 6,042,847 A | 3/2000 | Kerc et al. | |
| 6,045,829 A | 4/2000 | Liversidge et al. | |
| 6,051,253 A | 4/2000 | Zettler et al. | |
| 6,063,821 A | 5/2000 | Breitenbach et al. | |
| 6,066,334 A | 5/2000 | Kolter et al. | |
| 6,071,539 A | 6/2000 | Robinson et al. | |
| 6,083,518 A | 7/2000 | Lindahl | |
| 6,113,941 A | 9/2000 | Takada et al. | |
| 6,120,802 A | 9/2000 | Breitenbach et al. | |
| 6,132,659 A | 10/2000 | Rosenberg et al. | |
| 6,136,346 A | 10/2000 | Eljamal et al. | |
| 6,150,424 A | 11/2000 | Breitenbach et al. | |
| 6,162,467 A | 12/2000 | Miller et al. | |
| 6,187,342 B1 | 2/2001 | Zeidler et al. | |
| 6,197,781 B1 | 3/2001 | Guitard et al. | |
| 6,197,787 B1 | 3/2001 | Franson et al. | |
| 6,207,197 B1 | 3/2001 | Illum et al. | |
| 6,221,368 B1 | 4/2001 | Breitenbach et al. | |
| 6,221,399 B1 | 4/2001 | Rolfes et al. | |
| 6,232,333 B1 | 5/2001 | Lipari et al. | |
| 6,248,363 B1 | 6/2001 | Patel et al. | |
| 6,248,775 B1 | 6/2001 | Vazquez et al. | |
| 6,251,434 B1 | 6/2001 | Breitenbach et al. | |
| 6,261,599 B1 | 7/2001 | Oshlack et al. | |
| 6,264,981 B1 | 7/2001 | Zhang et al. | |
| 6,268,207 B1 | 7/2001 | Bailey | |
| 6,271,307 B1 | 8/2001 | Huff et al. | |
| 6,274,727 B1 | 8/2001 | Maul et al. | |
| 6,281,282 B1 | 8/2001 | Breitenbach et al. | |
| 6,284,270 B1 | 9/2001 | Lagoviyer et al. | |
| 6,284,803 B1 | 9/2001 | Kothrade et al. | |
| 6,290,990 B1 | 9/2001 | Grabowski et al. | |
| 6,294,192 B1 | 9/2001 | Patel et al. | |
| 6,312,726 B1 | 11/2001 | Nakamichi et al. | |
| 6,318,650 B1 | 11/2001 | Breitenbach et al. | |
| 6,319,520 B1 | 11/2001 | Wuthrich et al. | |
| 6,322,816 B1 | 11/2001 | Zeidler et al. | |
| 6,333,048 B1 | 12/2001 | Asmussen et al. | |
| 6,350,398 B1 | 2/2002 | Breitenbach et al. | |
| 6,372,259 B1 | 4/2002 | Kumar | |
| 6,372,905 B1 * | 4/2002 | Chemburkar et al. | 544/316 |
| 6,379,707 B2 | 4/2002 | Vladyka, Jr. et al. | |
| 6,383,471 B1 | 5/2002 | Chen et al. | |
| 6,387,401 B2 | 5/2002 | Rosenberg et al. | |
| 6,391,338 B1 | 5/2002 | Frisbee et al. | |
| 6,423,256 B1 | 7/2002 | Kothrade et al. | |
| 6,436,440 B1 | 8/2002 | Meffert et al. | |
| 6,440,946 B1 * | 8/2002 | Kiso et al. | 514/45 |
| 6,451,339 B2 | 9/2002 | Patel et al. | |
| 6,462,093 B1 | 10/2002 | Miyamoto et al. | |
| 6,465,010 B1 | 10/2002 | Lagoviyer et al. | |
| 6,465,011 B2 | 10/2002 | Law et al. | |
| 6,488,939 B1 | 12/2002 | Zeidler et al. | |
| 6,488,961 B1 | 12/2002 | Robinson et al. | |
| 6,488,963 B1 | 12/2002 | McGinity et al. | |
| 6,497,905 B1 | 12/2002 | Vladyka, Jr. et al. | |
| 6,511,681 B2 | 1/2003 | Vladyka, Jr. et al. | |
| 6,528,089 B1 | 3/2003 | Kothrade et al. | |
| 6,541,030 B2 | 4/2003 | Vaghefi | |
| 6,541,034 B1 | 4/2003 | Gergely et al. | |
| 6,547,997 B1 | 4/2003 | Breitenbach et al. | |
| 6,569,455 B1 | 5/2003 | Kanikanti et al. | |
| 6,576,255 B1 | 6/2003 | Petereit et al. | |
| 6,579,521 B2 * | 6/2003 | Sahner | 424/85.2 |
| 6,599,528 B1 * | 7/2003 | Rosenberg et al. | 424/451 |
| 6,599,931 B1 | 7/2003 | Breitenbach et al. | |
| 6,608,198 B2 * | 8/2003 | Dickman et al. | 544/316 |
| 6,610,764 B1 | 8/2003 | Martin et al. | |
| 6,632,389 B1 | 10/2003 | Ernst et al. | |
| 6,632,455 B2 | 10/2003 | Sangekar et al. | |
| 6,649,186 B1 | 11/2003 | Robinson et al. | |
| 6,669,879 B1 | 12/2003 | Spengler et al. | |
| 6,669,883 B1 | 12/2003 | Rosenberg et al. | |
| 6,677,362 B1 | 1/2004 | Ghebre-Sellassie et al. | |
| 6,692,767 B2 | 2/2004 | Burnside et al. | |
| 6,703,403 B2 | 3/2004 | Norbeck et al. | |
| 6,706,281 B2 | 3/2004 | Oshlack et al. | |
| 6,706,283 B1 | 3/2004 | Appel et al. | |
| 6,713,081 B2 | 3/2004 | Robinson et al. | |
| 6,730,319 B2 | 5/2004 | Maeder et al. | |
| 6,733,781 B2 | 5/2004 | Abu-Izza et al. | |
| 6,737,005 B1 | 5/2004 | Rosenberg et al. | |
| 6,743,442 B2 | 6/2004 | Oshlack et al. | |
| 6,763,607 B2 | 7/2004 | Beyerinck et al. | |
| 6,787,157 B1 | 9/2004 | Rosenberg et al. | |
| 6,805,881 B1 | 10/2004 | Kanikanti et al. | |
| 6,834,310 B2 | 12/2004 | Munger et al. | |
| 6,872,336 B2 | 3/2005 | Tanno et al. | |
| 6,894,171 B1 | 5/2005 | Bauer et al. | |
| 6,899,899 B2 | 5/2005 | Takagi et al. | |
| 6,923,988 B2 | 8/2005 | Patel et al. | |
| 6,973,741 B2 | 12/2005 | Beyerinck et al. | |
| 6,982,094 B2 | 1/2006 | Sowden | |
| 7,014,810 B2 | 3/2006 | Krull et al. | |
| 7,022,344 B1 | 4/2006 | Kothrade et al. | |
| 7,122,143 B2 | 10/2006 | Sowden et al. | |
| 7,148,359 B2 | 12/2006 | Chemburkar et al. | |
| 7,229,641 B2 | 6/2007 | Cherukuri | |
| 7,235,260 B2 | 6/2007 | Crew et al. | |
| 7,282,218 B2 | 10/2007 | Kulkarni et al. | |
| 7,297,345 B2 | 11/2007 | Sowden | |
| 7,364,752 B1 | 4/2008 | Fort et al. | |
| 7,407,670 B2 | 8/2008 | Six et al. | |
| 7,413,690 B1 | 8/2008 | Cheboyina et al. | |
| 7,419,685 B2 | 9/2008 | Kothrade et al. | |
| 7,491,407 B2 | 2/2009 | Pourdeyhimi et al. | |
| 7,550,158 B2 | 6/2009 | Appel et al. | |
| 7,645,474 B1 | 1/2010 | Pathak et al. | |
| 7,687,071 B1 | 3/2010 | Heger et al. | |
| 7,727,551 B2 | 6/2010 | Massironi | |
| 7,771,632 B2 | 8/2010 | Ghebre-Sellassie et al. | |
| 7,780,988 B2 | 8/2010 | Beyerinck et al. | |
| 7,785,512 B1 | 8/2010 | Pathak | |
| 7,846,477 B2 | 12/2010 | Rosenberg et al. | |
| 7,867,517 B2 | 1/2011 | Massironi | |
| 7,887,840 B2 | 2/2011 | Curatolo et al. | |
| 7,923,026 B2 | 4/2011 | Moschwitzer | |
| 7,951,401 B2 | 5/2011 | Colombo et al. | |
| 7,968,120 B2 | 6/2011 | Li et al. | |
| 7,972,624 B2 | 7/2011 | Li et al. | |
| 2001/0006650 A1 | 7/2001 | Burnside et al. | |
| 2001/0006677 A1 | 7/2001 | McGinity et al. | |
| 2001/0038852 A1 | 11/2001 | Kolter et al. | |
| 2001/0039551 A1 | 11/2001 | Saito et al. | |
| 2001/0044409 A1 | 11/2001 | Ghebre-Sellassie et al. | |
| 2001/0048946 A1 | 12/2001 | Ghebre-Sellassie | |
| 2001/0051721 A1 | 12/2001 | Dickman et al. | |
| 2002/0001617 A1 | 1/2002 | Lee et al. | |
| 2002/0006443 A1 | 1/2002 | Curatolo et al. | |
| 2002/0009494 A1 | 1/2002 | Curatolo et al. | |
| 2002/0015731 A1 | 2/2002 | Appel et al. | |
| 2002/0031547 A1 | 3/2002 | Takagi et al. | |
| 2002/0044968 A1 | 4/2002 | Van Lengerich | |
| 2002/0102300 A1 | 8/2002 | Miller et al. | |
| 2002/0114833 A1 | 8/2002 | Abu-Izza et al. | |
| 2002/0122825 A1 | 9/2002 | Hinrichs et al. | |
| 2002/0142043 A1 | 10/2002 | Kato et al. | |
| 2002/0160042 A1 | 10/2002 | Petereit et al. | |
| 2002/0161884 A1 | 10/2002 | Munger et al. | |
| 2002/0187188 A1 | 12/2002 | Cherukuri | |
| 2002/0198160 A1 * | 12/2002 | Everitt et al. | 514/43 |
| 2003/0015814 A1 | 1/2003 | Kurll et al. | |
| 2003/0021840 A1 | 1/2003 | Infeld et al. | |
| 2003/0021842 A1 | 1/2003 | Lagoviyer et al. | |
| 2003/0039686 A1 | 2/2003 | Maeder et al. | |
| 2003/0054038 A1 | 3/2003 | Crew et al. | |
| 2003/0059468 A1 | 3/2003 | Mattern et al. | |
| 2003/0064108 A1 | 4/2003 | Lukas et al. | |
| 2003/0072801 A1 | 4/2003 | Curatolo et al. | |
| 2003/0086976 A1 | 5/2003 | Hayes et al. | |
| 2003/0091626 A1 | 5/2003 | Katsuta | |
| 2003/0091630 A1 | 5/2003 | Louie-Helm et al. | |
| 2003/0091643 A1 | 5/2003 | Friesen et al. | |
| 2003/0096791 A1 | 5/2003 | Gupte et al. | |
| 2003/0099690 A1 | 5/2003 | Awamura et al. | |
| 2003/0099703 A1 | 5/2003 | Aoki | |

| | | | | | | |
|---|---|---|---|---|---|---|
| 2003/0099708 A1 | 5/2003 | Rowe et al. | | 2005/0031693 A1 | 2/2005 | Babcock et al. |
| 2003/0104063 A1 | 6/2003 | Babcock et al. | | 2005/0031696 A1 | 2/2005 | Kolhe et al. |
| 2003/0104065 A1 | 6/2003 | Brodin et al. | | 2005/0042293 A1 | 2/2005 | Jackson et al. |
| 2003/0104068 A1 | 6/2003 | Mathiowitz et al. | | 2005/0048112 A1 | 3/2005 | Breitenbach et al. |
| 2003/0109639 A1 | 6/2003 | Lippold et al. | | 2005/0048116 A1 | 3/2005 | Straub et al. |
| 2003/0129250 A1 | 7/2003 | Batycky et al. | | 2005/0058705 A1 | 3/2005 | Remon et al. |
| 2003/0133984 A1 | 7/2003 | Ambühl et al. | | 2005/0058710 A1 | 3/2005 | Straub et al. |
| 2003/0141378 A1 | 7/2003 | Raehse et al. | | 2005/0079138 A1 | 4/2005 | Chickering, III et al. |
| 2003/0147965 A1 | 8/2003 | Bassett et al. | | 2005/0084529 A1 | 4/2005 | Rosenberg et al. |
| 2003/0152619 A1 | 8/2003 | Stevens et al. | | 2005/0089568 A1 | 4/2005 | Oshlack et al. |
| 2003/0153608 A1 | 8/2003 | Maegerlein et al. | | 2005/0100586 A1 | 5/2005 | Sournac et al. |
| 2003/0161884 A1 | 8/2003 | Rosenberg et al. | | 2005/0100598 A1 | 5/2005 | Mizumoto et al. |
| 2003/0170309 A1 | 9/2003 | Babcock et al. | | 2005/0106257 A1 | 5/2005 | Albayrak |
| 2003/0203027 A1 | 10/2003 | Verreck et al. | | 2005/0143404 A1 | 6/2005 | Rosenberg et al. |
| 2003/0206947 A1 | 11/2003 | Kanikanti et al. | | 2005/0158385 A1 | 7/2005 | Verreck et al. |
| 2003/0206978 A1 | 11/2003 | Sherwood et al. | | 2005/0158386 A1 | 7/2005 | Tanno et al. |
| 2003/0211168 A1 | 11/2003 | Lynenskjold et al. | | 2005/0163852 A1 | 7/2005 | Bresciani et al. |
| 2003/0211197 A1 | 11/2003 | Burkle et al. | | 2005/0163853 A1 | 7/2005 | Szente et al. |
| 2003/0212102 A1 | 11/2003 | Koretke et al. | | 2005/0169988 A1 | 8/2005 | Tao et al. |
| 2003/0219489 A1 | 11/2003 | Curatolo et al. | | 2005/0175687 A1 | 8/2005 | McAllister et al. |
| 2003/0224043 A1 | 12/2003 | Appel et al. | | 2005/0202090 A1 | 9/2005 | Clarke |
| 2003/0228358 A1 | 12/2003 | Perlman et al. | | 2005/0245483 A1 | 11/2005 | Brogmann et al. |
| 2004/0001888 A1 | 1/2004 | Jin | | 2005/0281876 A1 | 12/2005 | Li et al. |
| 2004/0009222 A1 | 1/2004 | Chou et al. | | 2006/0003011 A1 | 1/2006 | Crew et al. |
| 2004/0013697 A1 | 1/2004 | Berndl et al. | | 2006/0003942 A1 | 1/2006 | Tung et al. |
| 2004/0013734 A1 | 1/2004 | Babcock et al. | | 2006/0013869 A1 | 1/2006 | Ignatious et al. |
| 2004/0013735 A1 | 1/2004 | Martin-Letellier et al. | | 2006/0029678 A1 | 2/2006 | Deghenghi |
| 2004/0013736 A1 | 1/2004 | Nakano et al. | | 2006/0034887 A1 | 2/2006 | Pelissier |
| 2004/0014817 A1 | 1/2004 | Rosenberg et al. | | 2006/0051412 A1 | 3/2006 | Petereit et al. |
| 2004/0024031 A1 | 2/2004 | Morissette et al. | | 2006/0073203 A1 | 4/2006 | Ljusberg-Wahren et al. |
| 2004/0029892 A1 | 2/2004 | Rosenberg et al. | | 2006/0078609 A1 | 4/2006 | Vandecruys et al. |
| 2004/0044196 A1 | 3/2004 | Davidson et al. | | 2006/0115539 A1 | 6/2006 | Prasch |
| 2004/0062778 A1 | 4/2004 | Shefer et al. | | 2006/0134203 A1 | 6/2006 | Ambuhl et al. |
| 2004/0062802 A1 | 4/2004 | Hermelin | | 2006/0147538 A1 | 7/2006 | Craig et al. |
| 2004/0067256 A1 | 4/2004 | Juppo | | 2006/0177496 A1 | 8/2006 | McAllister et al. |
| 2004/0076673 A1 | 4/2004 | Bateman et al. | | 2006/0204577 A1 | 9/2006 | Crew et al. |
| 2004/0081694 A1 | 4/2004 | Oshlack et al. | | 2006/0216351 A1 | 9/2006 | Friesen et al. |
| 2004/0081701 A1 | 4/2004 | Erkoboni et al. | | 2006/0251724 A1 | 11/2006 | Farrell et al. |
| 2004/0086569 A1 | 5/2004 | Sparer et al. | | 2006/0257470 A1 | 11/2006 | Rosenberg et al. |
| 2004/0091529 A1 | 5/2004 | Edgren et al. | | 2006/0269608 A1 | 11/2006 | Abu Shmeis-Ziadeh et al. |
| 2004/0096499 A1 | 5/2004 | Vaya et al. | | 2006/0286169 A1 | 12/2006 | Leigh et al. |
| 2004/0104501 A1 | 6/2004 | Petereit et al. | | 2007/0009592 A1 | 1/2007 | Remon et al. |
| 2004/0110694 A1 | 6/2004 | Ghebre-Sellassie et al. | | 2007/0014856 A1 | 1/2007 | Takagi et al. |
| 2004/0115256 A1 | 6/2004 | MacAllister et al. | | 2007/0031501 A1 | 2/2007 | Van Es et al. |
| 2004/0115273 A1 | 6/2004 | Sparer et al. | | 2007/0042044 A1 | 2/2007 | Fischer et al. |
| 2004/0120927 A1 | 6/2004 | Nathan | | 2007/0053978 A1 | 3/2007 | Sherwood et al. |
| 2004/0138231 A1 | 7/2004 | Bateman et al. | | 2007/0077305 A1 | 4/2007 | Le et al. |
| 2004/0146550 A1 | 7/2004 | Ng et al. | | 2007/0098795 A1 | 5/2007 | Miller et al. |
| 2004/0151056 A1 | 8/2004 | Omtveit et al. | | 2007/0122482 A1 | 5/2007 | Holm et al. |
| 2004/0154317 A1 | 8/2004 | Shekunov et al. | | 2007/0134336 A1 | 6/2007 | Worle et al. |
| 2004/0156894 A1 | 8/2004 | Grother et al. | | 2007/0249643 A1 | 10/2007 | Rosenberg et al. |
| 2004/0156905 A1 | 8/2004 | Babcock et al. | | 2007/0249692 A1 | 10/2007 | Fort et al. |
| 2004/0166153 A1 | 8/2004 | McAllister et al. | | 2007/0275058 A1 | 11/2007 | Tanaka et al. |
| 2004/0185112 A1 | 9/2004 | Beyerinck et al. | | 2007/0287664 A1 | 12/2007 | Ralston, II et al. |
| 2004/0185170 A1 | 9/2004 | Chungi et al. | | 2007/0298116 A1 | 12/2007 | Bechtold-Peters et al. |
| 2004/0194338 A1 | 10/2004 | Beyerinck et al. | | 2008/0038340 A1 | 2/2008 | Kusaki et al. |
| 2004/0197411 A1 | 10/2004 | Gao et al. | | 2008/0063708 A1 | 3/2008 | Perlman et al. |
| 2004/0197414 A1 | 10/2004 | Ahola et al. | | 2008/0138419 A1 | 6/2008 | Liao et al. |
| 2004/0198645 A1 | 10/2004 | Ambühl et al. | | 2008/0153925 A1 | 6/2008 | Pierobon et al. |
| 2004/0198901 A1 | 10/2004 | Graham et al. | | 2008/0181948 A1 | 7/2008 | Berndl et al. |
| 2004/0219222 A1 | 11/2004 | Sjoblom | | 2008/0187612 A1 | 8/2008 | Kannar et al. |
| 2004/0220081 A1 | 11/2004 | Kreitz et al. | | 2008/0199516 A1 | 8/2008 | McAllister |
| 2004/0228916 A1 | 11/2004 | Tanno et al. | | 2008/0206349 A1 | 8/2008 | Barnwell et al. |
| 2004/0234597 A1 | 11/2004 | Shefer et al. | | 2008/0206350 A1 | 8/2008 | Gryczke |
| 2004/0234673 A1 | 11/2004 | Letavernier et al. | | 2008/0213371 A1 | 9/2008 | Jain et al. |
| 2004/0247624 A1 | 12/2004 | Unger et al. | | 2008/0234352 A1 | 9/2008 | Fischer et al. |
| 2004/0247666 A1 | 12/2004 | Massironi | | 2008/0241261 A1 | 10/2008 | Kolter et al. |
| 2004/0247687 A1 | 12/2004 | Petereit et al. | | 2008/0248107 A1 | 10/2008 | Pilgaonkar et al. |
| 2004/0253314 A1 | 12/2004 | Petereit et al. | | 2008/0254124 A1 | 10/2008 | Bar-Shalom |
| 2004/0258752 A1 | 12/2004 | Paruthi et al. | | 2008/0260814 A1 | 10/2008 | Petereit et al. |
| 2004/0265378 A1 | 12/2004 | Peng et al. | | 2008/0260835 A1 | 10/2008 | Hayes et al. |
| 2005/0003004 A1 | 1/2005 | Vehring et al. | | 2008/0292707 A1 | 11/2008 | Babcock et al. |
| 2005/0008697 A1 | 1/2005 | Gorissen | | 2008/0305168 A1 | 12/2008 | Moon et al. |
| 2005/0008706 A1 | 1/2005 | Holm et al. | | 2008/0317851 A1 | 12/2008 | Appel et al. |
| 2005/0013856 A1 | 1/2005 | Trivedi et al. | | 2009/0011024 A1 | 1/2009 | Babcock et al. |
| 2005/0014304 A1 | 1/2005 | Moon et al. | | 2009/0017125 A1 | 1/2009 | Lynenskjold et al. |
| 2005/0025791 A1 | 2/2005 | Remenar et al. | | 2009/0036551 A1 | 2/2009 | Venkatesh et al. |
| 2005/0031691 A1 | 2/2005 | McGurk et al. | | 2009/0053317 A1 | 2/2009 | Vigo et al. |
| 2005/0031692 A1 | 2/2005 | Beyerinck et al. | | 2009/0104269 A1 | 4/2009 | Graham et al. |

| | | | | | | |
|---|---|---|---|---|---|---|
| 2009/0148517 | A1 | 6/2009 | Oshlack et al. | EP | 942721 B1 | 1/2003 |
| 2009/0218731 | A1 | 9/2009 | Rogasch et al. | EP | 864324 B1 | 10/2003 |
| 2009/0258953 | A1 | 10/2009 | Dobrawa et al. | EP | 0 852 140 | 12/2003 |
| 2009/0263479 | A1 | 10/2009 | Moschwitzer et al. | EP | 864326 B1 | 6/2004 |
| 2009/0304795 | A1 | 12/2009 | Bernigal et al. | EP | 1 227 797 | 1/2005 |
| 2009/0324694 | A1 | 12/2009 | Mohammad | EP | 1 175 205 | 6/2006 |
| 2010/0010101 | A1 | 1/2010 | Cherukuri | EP | 2311435 A1 | 4/2011 |
| 2010/0062073 | A1 | 3/2010 | Beyerinck et al. | GB | 2011382 A | 7/1979 |
| 2010/0068268 | A1 | 3/2010 | Rahmouni et al. | GB | 2 053 681 | 11/1981 |
| 2010/0112050 | A1 | 5/2010 | Ryoo et al. | GB | 2011382 B | 8/1982 |
| 2010/0137455 | A1 | 6/2010 | Bouillo et al. | GB | 2173703 A | 10/1986 |
| 2010/0166857 | A1 | 7/2010 | Yan et al. | JP | 61205208 A | 9/1986 |
| 2010/0172974 | A1 | 7/2010 | Oshlack et al. | JP | 61243012 A | 10/1986 |
| 2010/0179182 | A1 | 7/2010 | Shmeis et al. | JP | 6048920 A | 2/1994 |
| 2010/0204259 | A1 | 8/2010 | Tygesen et al. | WO | WO8905138 A1 | 6/1989 |
| 2010/0204425 | A1 | 8/2010 | Mertoglu et al. | WO | 90/06115 | 6/1990 |
| 2010/0215753 | A1 | 8/2010 | Sherwood et al. | WO | WO9118613 A1 | 12/1991 |
| 2010/0222220 | A1 | 9/2010 | Hanna et al. | WO | WO9307859 A1 | 4/1993 |
| 2010/0247612 | A1 | 9/2010 | Fuisz | WO | WO9311749 A1 | 6/1993 |
| 2010/0256110 | A1 | 10/2010 | Babcock et al. | WO | WO9315736 A1 | 8/1993 |
| 2011/0008430 | A1 | 1/2011 | Rosenberg et al. | WO | WO9320138 A2 | 10/1993 |
| 2011/0015216 | A1 | 1/2011 | Berndl et al. | WO | 95/07696 | 3/1995 |
| 2011/0020455 | A1 | 1/2011 | Yoshida et al. | WO | WO9509614 A1 | 4/1995 |
| 2011/0091546 | A1 | 4/2011 | Tanaka et al. | WO | 95/22319 | 8/1995 |
| 2011/0123652 | A1 | 5/2011 | Berndl et al. | WO | WO9600179 A1 | 1/1996 |
| 2011/0217381 | A1 | 9/2011 | Angus et al. | WO | WO9619962 A1 | 7/1996 |
| 2011/0236443 | A1 | 9/2011 | Hall et al. | WO | WO9619963 A1 | 7/1996 |
| 2011/0244002 | A1 | 10/2011 | Shen et al. | WO | WO9623499 A1 | 8/1996 |
| 2011/0250269 | A1 | 10/2011 | Xu et al. | WO | WO9636318 A2 | 11/1996 |
| 2011/0277339 | A1 | 11/2011 | Beyerinck et al. | WO | 97/01349 | 1/1997 |
| 2011/0288181 | A1 | 11/2011 | Koltzenburg et al. | WO | WO9706781 A1 | 2/1997 |
| 2011/0311595 | A1 | 12/2011 | Berndl et al. | WO | WO9713503 A1 | 4/1997 |
| | | | | WO | 97/21685 | 6/1997 |
| | | FOREIGN PATENT DOCUMENTS | | WO | WO9734645 A1 | 9/1997 |
| | | | | WO | 97/44014 | 11/1997 |
| CA | | 2096969 C | 5/1992 | WO | WO9746222 A1 | 12/1997 |
| CA | | 2227272 A1 | 3/1997 | WO | 98/07429 | 2/1998 |
| CA | | 2 343 234 | 3/2000 | WO | 98/22106 | 5/1998 |
| CA | | 2 352 874 | 6/2000 | WO | WO9822094 A2 | 5/1998 |
| CA | | 2 367 020 | 9/2000 | WO | 98/24430 | 6/1998 |
| CA | | 2 368 625 | 10/2000 | WO | WO9938496 A1 | 8/1999 |
| CA | | 2 374 931 | 1/2001 | WO | WO9955774 A1 | 11/1999 |
| CA | | 2408915 | 11/2002 | WO | WO9963841 A1 | 12/1999 |
| CA | | 2 479 749 | 10/2003 | WO | WO0000179 A1 | 1/2000 |
| CA | | 2 501 245 | 4/2004 | WO | WO0040220 A1 | 7/2000 |
| CA | | 2 568 378 | 12/2005 | WO | 00/57854 | 10/2000 |
| CA | | 2229650 C | 8/2006 | WO | 00/74677 | 12/2000 |
| DE | | 973095 C | 12/1959 | WO | 01/00175 | 1/2001 |
| DE | | 19536387 A1 | 4/1997 | WO | 01/22938 | 4/2001 |
| DE | | 19629753 A1 | 1/1998 | WO | 01/23362 | 4/2001 |
| DE | | 19637479 A1 | 3/1998 | WO | 01/34118 | 5/2001 |
| EP | | 0240904 A2 | 10/1987 | WO | 01/34119 | 5/2001 |
| EP | | 0240906 A2 | 10/1987 | WO | WO0134119 A2 | 5/2001 |
| EP | | 252886 A2 | 1/1988 | WO | 01/52821 | 7/2001 |
| EP | | 0 414 422 | 2/1991 | WO | 01/91727 | 12/2001 |
| EP | | 421581 A1 | 4/1991 | WO | WO0203955 A1 | 1/2002 |
| EP | | 421582 A1 | 4/1991 | WO | WO0205788 A1 | 1/2002 |
| EP | | 240906 B1 | 5/1991 | WO | 02/20057 | 3/2002 |
| EP | | 0435450 A2 | 7/1991 | WO | WO0235991 A2 | 5/2002 |
| EP | | 0272336 B1 | 10/1991 | WO | WO0238126 A2 | 5/2002 |
| EP | | 240904 B1 | 7/1992 | WO | WO0245696 A1 | 6/2002 |
| EP | | 0570327 A1 | 11/1993 | WO | 02/092595 | 11/2002 |
| EP | | 358105 B1 | 3/1994 | WO | WO02089835 A2 | 11/2002 |
| EP | | 414422 B1 | 4/1994 | WO | 02/096395 | 12/2002 |
| EP | | 732923 A1 | 9/1996 | WO | 03/006382 | 1/2003 |
| EP | | 852140 A1 | 7/1998 | WO | 03/006383 | 1/2003 |
| EP | | 0 864 324 | 9/1998 | WO | WO03047551 A1 | 6/2003 |
| EP | | 0 864 326 | 9/1998 | WO | WO03063833 A1 | 8/2003 |
| EP | | 942721 A1 | 9/1999 | WO | 03/080120 | 10/2003 |
| EP | | 0551820 B1 | 11/1999 | WO | 2004/032903 | 4/2004 |
| EP | | 0 988 106 | 3/2000 | WO | 2004/039349 | 5/2004 |
| EP | | 1003485 A1 | 5/2000 | WO | 2004/050068 | 6/2004 |
| EP | | 1027886 A2 | 8/2000 | WO | 2004/054568 | 7/2004 |
| EP | | 1027887 A2 | 8/2000 | WO | WO2004062643 A1 | 7/2004 |
| EP | | 1070496 A1 | 1/2001 | WO | WO2004100930 A1 | 11/2004 |
| EP | | 988106 B1 | 8/2001 | WO | WO2004112755 A1 | 12/2004 |
| EP | | 0732923 | 12/2001 | WO | 2005/004836 | 1/2005 |
| EP | | 1175205 A2 | 1/2002 | WO | 2005/007139 | 1/2005 |
| EP | | 1227797 A2 | 8/2002 | WO | WO2005007070 A2 | 1/2005 |
| EP | | 0942721 | 1/2003 | | | |

| WO | WO2005035514 A2 | 4/2005 |
| WO | WO2005039551 A2 | 5/2005 |
| WO | WO2006091529 A2 | 8/2006 |
| WO | WO2007002041 A2 | 1/2007 |
| WO | WO2007050631 A2 | 5/2007 |
| WO | WO2010017053 A1 | 2/2010 |
| WO | WO2011090724 A2 | 7/2011 |
| WO | WO2011159626 A1 | 12/2011 |
| ZA | 9608134 | 3/1998 |
| ZA | 9608134 A | 3/1998 |
| ZA | 9708219 | 12/1999 |

OTHER PUBLICATIONS

Karanth, H, et al., "Industrially Feasible Alternative Approaches in the Manufacture of Solid Dispersions: A Technical Report", *AAPS PharmSciTech*, 7(4):Art. 87 (2006).

Law, D., et al., "Physiochemical Considerations in the Preparation of Amorphous Ritonavir-Poly(ethylene glycol) 8000 Solida Dispersions", *J. of Pharmaceutical Sci.*, 90(8):1015-1025 (2001).

Aungst et al., "Amphiphilic vehicles improve the oral bioavailability of a poorly soluble HIV protease inhibitor at high doses," International Journal of Pharmaceutics 156:79-88 (1997).

Chiou et al., "Pharmaceutical applications of solid dispersion systems," J. Pharm. Sci. 60(9):1281-1302 (1971).

W. Awni, "Significantly Reduced Food Effect and Pharmacokinetic Variability with a Novel Looipinavir/ritonavir Table Formulation", Third IAS Conference on HIV Pathogenesis and Treatment, Jul. 24-27, 2005, Rio de Janeiro, Brazil.

International Search Report & Written Opinion from PCT/US2004/027401 dated May 8, 2006.

BASF Fine Chemicals, "ExAct Excipients & Actives for Pharma", *BASF*, 2:1-16 (1999).

Bouma, M.G., et al., "Novel Therapetic Delivery Systems",*J. of Contr. Rel.*, 87:199-308 (2003).

Breitenbach, J., "Melt Extrusion Can Bring New Benefits to HIV Therapy: The Example of Kaletra (R) Tablets", *Amer. :J. of Drug Deliv.*, 4(2):61-64 (2006).

Corrigan, O.I. & Healy, A.M., "Surfactants in Pharmaceutical Products and Systems", *Encycl. of Pharm. Tech.*, 2639-2653 (2002).

Hulsmann, S., et al., "Melt extrusion—an alternative method for enhancing the eissolution rate of 17β-estradiol hemihydrate", *Eur. J. of Pharm. & Biopharm.*, 49:237-242 (2000).

Law, D., et al., "Physicochemical Considerations in the Preparation of Amorphous Ritonavir-Poly(ethylene glycol) 8000 Solid Dispersions", *J. of Pharm. Sci.*, 90(8):1015-1025 (2001).

Law, D., et al., "Ritonavir-PEG 8000 Amorphous Solid Dispersions: In Vitro and In Vivo Evaluations", *J. of Pharm. Sci.*, 93(3):563-570 (2004).

Palmieri, G.F., et al., "Characterization and dissolution studies of PEG 4000/fenofibrate solid dispersions", *S.T.P. Pharma Sci.*, 6(3):188-194 (1996).

Serajuddin, A.T.M., "Solid Dispersioin of Poorly Water-Soluble Drugs: Early Promises, Subsequent Problems, and Recent Breakthroughs", *J. of Pharm. Sci.*, 88(10):1058-1066 (1999).

U.S. Appl. No. 09/438,994, James J. Fort, et al., filed Nov. 12, 1999.
U.S. Appl. No. 09/709,829, James J. Fort, et al., filed Nov. 10, 2000.
U.S. Appl. No. 11/691,819, James J. Fort, et al., filed Mar. 27, 2007.
U.S. Appl. No. 11/773,185 Joerge Rosenberg, et al., filed Jul. 3, 2007.

Zhu, T., et al., New Tablet Formulation of Lopinavir/Ritonavir is Bioequivalent to the Capsule at a Dose of 800/200 mg?, *48th Int. Conf. on Antimic. Agents & Chem. (ICAAC)*, (2005).

Dias, L., et al., "Physical and Oral Dog Bioavailability Evaluatoins of ABT-538: PVP Co-Precipitates", Physical Research Suppl. (0724-8741), 13(9):S-351 PDD7475 (1996).

Dias, L., et al., "Physical and Oral Dog Bioavailability Evaluaiton of ABT-538: PVP Co-Precipitates", poster (1996).

Kempf, D.J., et al., "ABT-538 is a potent inhibitor of human immunodeficiency virus protease and has high oral bioavailability in humans", Proc. Natl. Acad. Sci. USA, 92:2484-2488 (1995).

Martin, D., et al., "Method of Preparing an Orally Bioavailable Solid Formulation of an Insoluble Protease Inhibitor as a Coprecipitate With PVP and Other Excipients", Pharmaceutical Research Suppl. (0724-8741), 13(9):S351 PDD 7474 (1996).

Martin, D., et al., "Method of Preparing an Orally Bioavailability Solid Formulation of an Insoluble Protease Inhibitor as a Coprecipitate with PVP and Other Excipients", Abbott Laboratories (1996).

Klein, Ce, et al, "The Effect of Food on Ritonavir Bioavailability Following Administration of Ritonavir 100 mg Film-Coated Tablet in Healthy Adult Subjects", Poster, Abbott Laboratories, Nov. 9-13, 2008.

Matrix Laboratories Opposition, Oct. 23, 2009, Matrix Laboratories.

Ansel C.H., et al., "Pharmaceutical Dosage Forms and Drug Delivery Systems", 7th Edition, Lippincott Williams & Wilkins, 1999, pp. 367-369.

Brazilian Interdisciplinary AIDS Association (ABIA) Opposition filed on Aug. 23, 2004, 26 pages.

CIPLA Pre-grant Oppositions Response mailed Aug. 11, 2011 for Indian Application No. 726/MUMNP/2009 filed Apr. 15, 2009.

Decision by Indian Patent Office dated Dec. 30, 2010.

European Search Report for Application No. EP10159672, mailed on May 26, 2010, 2 pages.

European Search Report for Application No. EP10181250, mailed on Dec. 10, 2010, 2 pages.

European Search Report for Application No. EP10181264, mailed on Dec. 10, 2010, 2 pages.

European Search Report for Application No. EP10181268, mailed on Dec. 10, 2010, 2 pages.

Final Office Action mailed Dec. 22, 2010 for U.S. Appl. No. 11/939,640, filed Nov. 14, 2007.

I-MAK Pre-Grant Opposition Response to Indian Patent Office for Application No. 339/MUMNP/2006 mailed Aug. 2, 2010. part-1-5.

IMAK Third Party Observation against EP Application No. 04816820.7 dated Oct. 25, 2010.

International Preliminary Report on Patentability and Written Opinion for Application No. PCT/US2006/005944, mailed on Aug. 28, 2007, 7 pages.

International Search Report for Application No. PCT/US2007/084617, mailed on Sep. 18, 2008, 3 pages.

Matrix Laboratories Pre-grant Opposition mailed Aug. 11, 2011 for Indian Application No. 726/MUMNP/2009 filed Apr. 15, 2009.

Mayersohn M., "Principles of Drug Absorption" in: Modern Pharmaceutics Drugs and the Pharmaceutical Sciences, Chapter 2, Banker G.S., et al., eds, 2002, pp. 23-66.

Non-Final Office Action mailed Apr. 8, 2010 for U.S. Appl. No. 11/939,640, filed Nov. 14, 2007.

Opposition Filed by Matrix Laboratories on Indian Application No. 676/MUMNP/2007 dated Apr. 28, 2011.

Opposition Filed by Matrix Laboratories on Indian Application No. 677/MUMNP/2007 dated Apr. 28, 2011.

Opposition Filed by Matrix Laboratories on Indian Application No. 1638 /MUMNP/2007 dated Apr. 28, 2011.

Order Granting Reexamination of US Patent No. 7364752 along with Reexam Non-Final Office Action dated Oct. 28, 2010.

ReExam—Non-Final Action mailed Oct. 28, 2010 for U.S. Appl. No. 95/000,568, filed Aug. 25, 2010.

ReExam Action Closing Prosecution mailed May 19, 2011 for U.S. Appl. No. 95/000,568, filed Aug. 25, 2010.

Request for Re-Examination on U.S. Appl. No. 95/000,568 (US7364752) mailed Aug. 25, 2010.

Response to Inter Partes Reexamination dated Jun. 17, 2011 for U.S. Appl. No. 95/000,568, filed Aug. 25, 2010.

Response to Office Action mailed Apr. 4, 2008 for European Application No. 04816820.7 filed Aug. 23, 2004.

Response to Office Action mailed Aug. 10, 2009 for European Application No. 04816820.7 filed Aug. 23, 2004.

Breitenbach J., et al., "Two Concepts, One Technology: Controlled-Release Solid Dispersions Using Melt Extrusion (Meltrex)," Drugs and the Pharmaceutical Sciences, 2008, vol. 183, pp. 179-185.

Buhler V., "Polyvinylpyrrolidone Excipients for Pharmaceuticals", Springer-Verlag, 2005, pp. 84-85, 92-93.

Eron J.J., et al., "Once-daily Versus Twice-daily Lopinavir/ritonavir in Antiretroviral-naive HIV-positive patients: a 48-week Randomized Clinical Trial," Journal of Infectious Diseases, 2004, vol. 189 (2), pp. 265-272.

Forster A., et al., "Characterization of Glass Solutions of Poorly Water-Soluble Drugs Produced by Melt Extrusion with Hydrophilic Amorphous Polymers," 2001, vol. 53 (3), pp. 303-315.

John M., et al., "Hepatitis C Virus-associated Hepatitis Following Treatment of HIV-infected Patients with HIV Protease Inhibitors: An Immune Restoration Disease", Aids, 1998, vol. 12 (17), pp. 2289-2293.

Rowe., "Polyoxyethylene Castor Oil Derivatives" Handbook of Pharmaceutical Excipients, 2002, pp. 474-478.

Royal, P.G., et al., "Characteristics of the Glass Transition of an Amorphous Drug Using Modulated DSC", Pharmaceutical Research, 15(7):1117-1121 (1998).

Sinha S., et al., "Solid Dispersion as an Approach for Bioavailability Enhancement of Poorly Water-Soluble Drug Ritonavir," AAPS PharmSciTech, 2010, vol. 11 (2), pp. 518-527.

Stenmark H.G., et al., "Biomimetic Synthesis of Macrolide/Ketolide Metabolites through a Selectiv N-Demethylation Reaction," Journal of Organic Chemistry, 2000, vol. 65 (12), pp. 3875-3876.

Thayer A. M., "Finding Solutions, Custom manufacturers take on drug solubility issues to help pharmaceutical firms move products through development," Chemical & Engineering News, 2010, vol. 88 (22), pp. 13-18.

Bachynsky, et al., Drug Dev. and Ind. Phar., 1997, vol. 23 (8), pp. 809-817.

Nakamichi K., et al. "Preparation of Nifedipine-Hydroxypropylmethylcellulose Phthalate Solid Dispersion by Twin Screw Extruder and its Evaluation," Yakuzaigaku, 1996, vol. 56 (1), pp. 15-22.

Non-Final Office Action mailed Oct. 12, 2011 for U.S. Appl. No. 12/899,227 filed Oct. 6, 2010.

Rodriguez-Espinosa C., et al., "Dissolution Kinetics for Coprecipitates of Diflunisal with PVP K30," European Journal of Drug Metabolism and Pharmacokinetics, 1998, vol. 23 (2), pp. 109-112.

Schwartz J.B., "Pharmaceutical Dosage Forms" vol. 2, Marcel Dekker, Inc., 1990, pp. 460-461.

Serajuddin, A.T.M., "Bioavailability Enhancement of Poorly Water-Soluble Drugs by Solid Dispersion in Surface Active and Self-Emulsifying Vehicles," B.T. Gattefosse, vol. 90, 43-50, 1997.

Voigt R., "Pharmaceutical Technology" for Students and Professionals, 7th revised Edition, 2000, pp. 80-85.

Ford, J.L., "The Current Status of Solid Dispersions", Pharm. Acta Helv., 61(3):69-88 (1986).

Physicians Desk Reference, online excert, PDR Electronic Libary.

Physicians Desk Reference, online . . . Norvir, Fenofibratre, and Greiseousulvin.

Opposition, Aug. 13, 2007, IMAK.

I-Mak Opposition, Sep. 10, 2007, IMAK.

CIPLA Opposition, Jul. 12, 2007, CIPLA.

Abbott 2007 Global Citizenship Report, Ingenuity at Work.

Abbott Laboratories: "Norvir" Product Labeling, NORVIR, Online, Mar. 2001.

Abbott Press Release, Jan. 24, 2007.

Abbott Press Release, Jan. 25, 2006.

Albers et al., "Mechanism of drug release from polymethacrylate-based extrudates and milled strands prepared by hot-melt extrusion," European Journal of Pharmaceutics and Biopharmaceutics, 2009, pp. 387-394, vol. 71.

Ambike et al., "Spray-Dried Amorphous Solid Dispersions of Simvastatin, a Low Tg Drug: In Vitro and In Vivo Evaluations," Pharmaceutical Research, 2005, pp. 990-998, vol. 22 (6).

Ambike et al., "Stability study of amorphous valdecoxib," International Journal of Pharmaceutics, 2004, pp. 151-162, vol. 282.

Bauer J. et al., "Ritonavir: An Extraordinary Example of Conformational Polymorphism," Pharmaceutical Research, vol. 18 (6), pp. 859-866, 2001.

Benet, "Using a Biopharmaceutics Drug Disposition Classification System to Predict Bioavailability and Eliminatiojn Characteristics of New Molecular Entities, http://www.njacs.org/drugmet_fall.html," NJ Drug Metabolism Discussion Group, 2006.

Boffito M. et al., "Clinical use of lopinavir/ritonavir in a salvage therapy setting: pharmacokinetics and pharmacodynamics," AIDS, 2002, vol. 16 (15), pp. 2081-2083.

Breitenbach Jorg et al., "Confocal Raman-Spectroscopy: Analytical Approach to Solid Dispersions and Mapping of Drugs," Pharm. Research, vol. 16 (7), pp. 1109-1113, 1999.

Center for Drug Evaluation and Research, Chemistry Reviews, 1999.

Office Action dated Mar. 19, 2008 for U.S. Appl. No. 10/925,442, filed Aug. 25, 2004.

Office Action dated Mar. 19, 2009 for U.S. Appl. No. 10/925,442, filed Aug. 25, 2004.

Corrigan et al., "Amorphous forms of thiazide diuretics prepared by spray-drying," International Journal 01 Pharmaceutics, 1984, pp. 195-200, vol. 18.

Corrigan et al., "Amorphous spray-dried hydrofiumethiazide-poly.mi ylpyrrolidone systems: physicochemical properties," J. Pharm. Pharmacol, 1984, pp. 217-221, vol. 36.

Corrigan et al., "Physicochemical Properties of Spray Dried Drugs: Phenobarbitone and Hydroflumethiazide," Drug Development and Industrial Pharmacy, 1983, pp. 1-20, vol. 9 (1&2).

Craig, "The mechanisms of drug release from solid dispersions in water-soluble polymers," International Journal of Pharmaceutics, 2002, pp. 131-144, vol. 231.

Custodio Joseph M. et al., "Predicting Drug Disposition, Absorption/Elimination/Transporter Interplay and the Role of Food on Drug Absorption," Adv. Drug Deliv Rev., vol. 60 (6), pp. 717-733, 2008.

Cvetkovic R. S. et al., "Lopinavir/ritonavir: a review of its use in the management of HIV infection," Drugs, 2003, vol. 63 (8), pp. 769-802.

Eagling V. A. et al., "Differential inhibition of cytochrome P450 isoforms by the protease inhibitors, ritonavir, saquinavir and indinavir," Br J Clin Pharmacol, vol. 44, pp. 190-194, 1997.

Excipients & Activities for Pharma, ExAct, No. 20, May 2008.

Formulation Technology, Emulsions, Suspensions, Solid Forms, Wiley-VCH, 2001, pp. 358-374.

Friesen et al., "Hydroxypropyl Methylcellulose Acetate Succinate-Based Spray-Dried Dispersions: An Overview," Molecular Pharmaceutics, 2008, pp. 1003-1019, vol. 5 (6).

Garren, et al, Bioavailability of Generic Ritonavir and Lopinavir/ritonavir Tablet Products in Dog Model, Abbott, 2009.

Gubbins P. O. et al., "Pharmacokinetics and safety of oral posaconazole in neutropenic stem cell transplant recipients," Antimicrob Agents Chemother, 2006, vol. 50 (6), pp. 1993-1999.

Hajratwala et al., "Effect of Aging on Hydrocortisone-Polyet hylene Glycol 4000 and Hydrocortisone-Polyvinylpyrrolidone Dispersions," Journal of Pharmaceutical Sciences, 1984, pp. 1539-1541, vol. 73 (11).

Hancock et al., "Characteristics and Significance of the Amorphous State in Pharmaceutical Systems," Journal of Pharmaceutical Sciences, 1997, pp. 1-12, vol. 86 (1).

Hancock et al., "Molecular Mobility of Amorphous Pharmaceutical Solids Below Their Glass Transition Temperatures," Pharmaceutical Research, 1995, pp. 799-806, vol. 12 (6).

Hasegawa et al., "Application of Solid Dispersions with Enteric Coating Agents to Overcome Some Pharmaceutical Problems," Chem. Pharm. Bull, 1986, pp. 2183-2190, vol. 34 (5).

Hasegawa et al., "Physical Properties of Solid Dispersions of Poorly Water-Soluble Drugs with Enteric Coating Agents1)," Chem. Pharm. Bull, 1985, pp. 3429-3435, vol. 33 (8).

Hasegawa et al., "Solid Dispersicn Obtained from Nifedipine and Enteric Coaling Agent. 1. Dissoluticn Behavicr," 1984, pp. 485-489, vol. 104.

Hasegawa et al., "Supersaturation Mechanism of Drugs from Solid Dispersions with Enteric Coating Agents," Chem. Pharm. Bull, 1988, pp. 4941-4950, vol. 36 (12).

Hicks C. et al., "Long-term safety and durable antiretroviral activity of lopinavir/ritonavir in treatment-naive patients: 4 year follow-up study," AIDS, 2004, vol. 18 (5), pp. 775-779.

IMAK Statement of Reply 339 MUM NP 2006 pp. 1-47.

IMAK Statement of Reply Exhibit D, Feb. 16, 2009, pp. 118-161.

IMAK Statement of Reply Exhibits A to C, Feb. 16, 2009, pp. 48-117.

IMAK Statement of Reply Exhibits E to O, Feb. 16, 2009, pp. 162-245.

IMAK Statement of Reply Exhibits P To R, Feb. 16, 2009, pp. 246-308.

International Search Report for application No. PCT/US06/005944, Mailed on Apr. 8, 2006, 3 pages.
Jachowicz et al., "Solid dispersions of oxazepam," International Journal of Pharmaceutics, 1993, pp. 321-325, vol. 99.
Kaletra 2000.
Kaletra 2005 tablet label.
Kanzer, J. et al., In situ formation of nanoparticles upon dispersion of melt extrudate formulations in aqueous medium assessed by asymmetrical flow field-flow fractionation, Journal of Pharmaceutical and Biomedical Analysis, 2010, doi:10.1016/j.jpba.2010.04.012.
Kaushal et al., "Amorphous Drug Delivery Systems: Molecular Aspects, Design, and Performance," Critical ReviewsTM in Therapeutic Drug Carrier Systems, 2004, pp. 133-193, vol. 21 (3).
Klein et al., "The Tablet Formulation of Lopinavir/Ritonavir Provides Similar Bioavailability to the Soft-Gelatin Capsule Formulation With Less Pharmacokinetic Variability and Diminished Food Effect," J Acquir Immune Defic Syndr, 2007, pp. 401-410, vol. 44 (4).
Konno et al., "Influence of Different Polymers on the Crystallization Tendency of Molecularly Dispersed Amorphous Felodipine," Journal of Pharmaceutical Sciences, 2006, pp. 2692-2705, vol. 95 (12).
Kumar G N et al., ""Cytochrome P450—Mediated Metabolism of the HIV-1 Protease Inhibitor Ritonavir (ABT-538) in Human Liver Microsomes"XP008024470," Journal of Pharmacology and Experimental Therapeutics, American Society for Pharmacology and, US, vol. 277(1), pp. 423-431, 1996.
Leuner C., et al., "Improving drug solubility for oral delivery using solid dispersions," European Journal of Pharmaceutics and Biopharmaceutics, 2000, 50, 47-60.
Lindenberg, Marc et al., "Classification of orally administered drugs on the World Health Organization Model list for Essential Medicines according to the biopharmaceutics classification system," E J of Pharma and Biopharm, vol. 58, pp. 265-278, 2004.
MatrixParagraph IV dated Jan. 29, 2009.
Miller et al., "Solid Dispersion Technologies," DrugsPharmSci, 2008, pp. 451-491, vol. 172.
Modern Pharmaceutics, Drugs and the Pharmaceutical Sciences, 2002, vol. 121, Chapter 11, pp. 335-380.
Modern Pharmaceutics, Drugs and the Pharmaceutical Sciences, 2002, vol. 121, Chapter 2, pp. 23-66.
Mooter et al., "Physical stabilisation of amorphous ketoconazole in solid dispersions with polyvinylpyrrolidone K25," European Journal of Pharmaceutical Sciences, 2001, pp. 261-269, vol. 12.
Morissette, Sherry L et al., "Elucidation of crystal form diversity of the HiV protease inhibitor ritonavir by highthroughput crystallization," PNAS, vol. 100 (5), pp. 2180-2184, 2003.
Mueller, "Badische Anilin- und Soda-Fabrik AG, Ludwigshafen/Rhein Untersuchungslaboratorium, Nachweis und Bestimmung von Polyvinylpyrrolidon (PVP) sowie Bestimmung von Wirkstoffen in PVP-haltigen Arzneimittelzubereitungen," Tica Acta Helvetiae, 1968, pp. 107-122, vol. 43.
Nakamichi et al., "The preparation of enteric solid dispersions with hydroxypropylmethylcellulose acetate succinate using a twin-screw extruder," J. Drug Del. Sci. Tech, 2004, pp. 193-198, vol. 14 (3).
Niazi, Sarfaraz K., Handbook of Pharmaceutical Manufacturing Formulations, Sompressed Solid Products vol. 1.
Office Action dated Jan. 10, 2007 for E.P. Serial No. 048168207 Filed Aug. 23, 2004.
Office Action dated Jan. 18, 2010 for U.S. Appl. No. 11/939,640, filed Nov. 14, 2007.
Office Action dated Jun. 22, 2009 for E.P. Serial No. 048168207 Filed Aug. 23, 2004.
Office Action dated Mar. 12, 2009 for U.S. Appl. No. 11/691,819, filed Mar. 27, 2007.
Office Action dated Mar. 17, 2010 for U.S. Appl. No. 12/190,252, filed Aug. 12, 2008.
Office Action dated May 13, 2009 for U.S. Appl. No. 12/190,252, filed Aug. 12, 2008.
Office Action dated May 19, 2008 for U.S. Appl. No. 11/691,819, filed Mar. 27, 2007.
Office Action dated Oct. 22, 2009 for U.S. Appl. No. 11/691,819, filed Mar. 27, 2007.
OKASA Opposition, Mar. 25, 2009, OKASA.

Otsuka et al., "Hygroscopic Stability and Dissolution Properties of Spray-Dried Solid Dispersions of Furosemide with Eudragit," Journal of Pharmaceutical Sciences, 1993, pp. 32-38, vol. 82 (1.
PCT International search report for application No. PCT/BR04/00119 mailed on Jan. 26, 2006, 1 page.
Peltonen et al., "Surface Pressure, Hysteresis, Interfacial Tension, and CMC of Four Sorbitan Monoesters at Water—Air, Water—Hexane, and Hexane—Air Interfaces," Journal of Colloid and Interface Science, 2000, pp. 1-6, vol. 227.
Pouton Colin W., "Formulation of poorly water-soluble drugs for oral administration: Physicochemical and physiological issues and the lipid formulation classification system," European J Pharm Sciences, vol. 29, pp. 278-287, 2006.
Qi et al., "Characterisation of solid dispersions of paracetamol and EUDRAGIT® E prepared by hot-melt extrusion using thermal, microthermal and spectroscopic analysis," International Journal of Pharmaceutics, 2008, pp. 158-167, vol. 354.
Rane et al., "Effect of Hydrophilic Swellable Polymers on Dissolution Enhancement of Carbamazepine Solid Dispersions Studied Using Response Surface Methodology," AAPS PharmSciTech, 2007, pp. E1-E11, vol. 8 (2).
Rosenberg et al., "Novel Therapeutic Delivery System," J of Controlled Release, vol. 87, pp. 264-267, 2003.
Rossie, Rochele C. et al., "Development and Validation of dissolution test for ritonavir soft gelatin capsules based on in vivo data," International Journal of Pharmaceutics, vol. 338, pp. 119-124, 2007.
Saez-Liorens X. et al., "Forty-eight-week evaluation of lopinavir/ritonavir, a new protease inhibitor, in human immunodeficiency virus-infected children," Pediatr Infect Dis J, 2003, vol. 22 (3), pp. 216-224.
Saleki-Gerhardt et al., "Non-Isothermal and Isothermal Crystallization of Sucrose from the Amorphous State," Pharmaceutical Research, 1994, pp. 1166-1173, vol. 11 (8).
Shamblin et al., "The Effects of Co-Lyophilized Polymeric Additives on the Glass 'Transition Temperature and Crystallization of Amorphous Sucrose," Journal of Thermal Analysis, 1996, pp. 1567-1579, vol. 47.
Simonelli et al., "Dissolution Rates of High Energy Polyvinylpyrrolidone (PVP) Sulfathiazole Coprecipitates," Jourirul of Pharmaceutical Sciences, 1969, pp. 538-549, vol. 58 (5).
Six et al., "Characterization of Solid Dispersions of Itraconazole and Hydroxypropylmethylcellulose Prepared by Melt Extrusion, Part II," Pharmaceutical Research, 2003, pp. 1047-1054, vol. 20 (7).
Takeuchi et al., "Spherical Solid Dispersion Containing Amorphous Tolbutamide Embedded in Enteric Coating Polymers or Colloid al Silica Prepared by Spray-Drying Technique," Chem. Pharm. Bull, 1987, pp. 3800-3806, vol. 35 ( 9 ).
Tanno et al., "Evaluation of Hypromellose Acetate Succinate (HPMCAS) as a Carrier in Solid Dispersions," Drug Development and Industrial Pharmacy, 2004, pp. 9-17, vol. 30 (1).
Teas, "Graphic Analysis of Resin Solubilities," Journal of Paint Technology, 1968, pp. 19-25, vol. 40 (516).
Tho, I. et al., Formation of nano/micro-dispersions with improved dissolution properties upon dispersion of ritonavir melt extrudate in aqueous media, European Journal of Pharmaceutical Sciences, 2010, doi: 10.1016/j/ ejps.2010.02.003.
U.S. Department of Health and Human Services Food and Drug Administration Center for Drug Evaluation and Research, Guidance for Industry, Aug. 2000, pp. 1-13.
Vasconcelos et al., "Solid dispersions as strategy to improve oral bioavailability of poor water soluble drugs," Drug Discovery Today, 2007, pp. 1068-1075, vol. 12 (23/24).
Verreck et al., "Characterization of solid dispersions of itraconazole and hydroxypropylmethylcellulose prepared by melt extrusion*/ part I," International Journal of Pharmaceutics, 2003, pp. 165-174, vol. 251.
Voigt R., et al., "Methods for determination of wett ability and their possible use in pharmaceutical technology", Pharmazie, 1975, 30 (11), 689-93.
Walmsley S. et al., "Lopinavir-ritonavir versus nelfinavir for the initial treatment of HIV infection," N Engl J Med, 2002, vol. 346 (26), pp. 2039-2046.

Yamagochi et al., "Improvement of Pharmaceutical Properties of 4"-O-(4-methoxyphenyl)acetyltylosin Using Solid Dispersion with Carboxymethylethylcellulose," Yakuzaigaku, 1993, pp. 221-228, vol. 53 (4).

Yu Lian, "Amorphous pharmaceutical solids: preparation, characterization and stabilization," Advanced Drug Delivery Reviews, 2001, pp. 27-42, vol. 48.

Zhou Deliang et al., "A Calorimetric Investigation of Thermodynamic and Molecular Mobility Contributions to the Physical Stability of Two Pharmaceutical Glasses," J Pharm. Sciences, vol. 96 (1), pp. 71-83, 2007.

Zhou Deliang et al., "Physical Stability of Amorphous Pharmaceuticals Importance of Configurational Thermodynamic Quantities and molecular Mobility," J Pharm Sciences, vol. 91 (8), pp. 1863-1872, 2002.

Co-Pending U.S. Appl. No. 12/880,781, filed Sep. 13, 2010.

Co-Pending U.S. Appl. No. 12/880,766, filed Sep. 13, 2010.

Breitenbach J., et al., "Two Concepts, One Technology: Controlled-Release Solid Dispersions with Meltrex," Drugs and the Pharmaceutical Sciences, 2003, pp. 125-134.

European Search Report for Application No. EP10184860, mailed on Dec. 6, 2010, 2 pages.

Franks F., "Scientific and Technological Aspects of Aqueous Glasses," Biophysical Chemistry, 2003, vol. 105 (2-3), pp. 251-261.

Herausgeber, "Chemie" Georg Thieme Verlag Stuttgart-NewYork, 1997, pp. 1549.

Kolter K., et al., "Hot-Melt Extrusion with BASF Pharma Polymers Extrusion Compendium," BASF—The Chemical Company, 2010, pp. 34-35.

Polymer Handbook, Brandrup J., et al., Eds., Interscience Publishers, 1975, Table of Contents.

Riesen R., et al., "The Glass Transition Temperature Measured by Different TA Techniques, Part 2: Determination of Glass Transition Temperatures," USERCOM, 2003, 5 pages.

Rosenberg J., et al., "Meltrex-Formulations Containing Solid Solutions of Nearly Insoluble Drugs: Formation of Nanoparticles on Dissolution in Water," 28th International Symposium on Controlled Release of Bioactive Materials, 2001, vol. 1, pp. 738-739.

Sjokvist E., et al., "Physicochemical Aspects of Drug Release. XIII. The effect of sodium dodecyl sulphate additions on the structure and Dissolution of a drug in solid dispersions," International Journal of Pharmaceutics, 1991, vol. 69, pp. 53-62.

Vadnere M.K., "Coprecipitates and Melts" in: Encyclopedia of Pharmaceutical Technology, 2nd Edition, Swarbrick J., eds., Marcel Dekker, Inc, 2002, vol. 1, pp. 641-648.

European Opposition to EP Patent No. 1663183 filed by F. Hoffmann-La Roche AG on Apr. 2, 2012.

European Opposition to EP Patent No. 1663183 filed by Generics (UK) Ltd. on Apr. 12, 2012.

European Opposition to EP Patent No. 1663183 filed by Teva Pharmaceuticals on Apr. 13, 2012.

European Opposition to EP Patent No. 1663183 filed by Hetero Drugs Ltd. on Apr. 13, 2012.

European Opposition to EP Patent No. 1663183 filed by Janssen on Apr. 13, 2012.

* cited by examiner

SOLID PHARMACEUTICAL DOSAGE FORMULATION

FIELD OF THE INVENTION

The present invention relates to a pharmaceutical dosage formulation, and more particularly, relates to a pharmaceutical dosage formulation comprising an HIV protease inhibitor.

BACKGROUND OF THE INVENTION

Millions of people around the world are suffering from HIV/AIDS, and millions more are likely to become infected each year. Many medications are currently available for the treatment of HIV/AIDS including HIV protease inhibitors (PI's), nucleoside/nucleotide reverse transcriptase inhibitors (NRTI's) and non-nucleoside reverse transcriptase inhibitors (NNRTI's). Most current treatment regimens require a combination of at least three medications, most commonly two NRTI's and either a PI or a NNRTI.

PI's are poorly soluble and are very difficult to formulate. Originally, PI's were provided as liquid formulations in which the PI component was dissolved. Currently, the most widely used PI dosage forms are gelatin capsules containing a fill solution in which the active ingredient is dissolved. The fill solutions required to dissolve the PI often contain excipients that cause discomfort or irritate the gastrointestinal system. Furthermore, only a limited amount of the PI can be dissolved in these dosage forms which therefore limits the amount of the PI loaded in each gelatin capsule.

In order to obtain the necessary dose of an individual PI, a patient must take several gelatin capsules at any given dosing period, which is repeated several times in a day. As mentioned above, therapy for HIV patients includes multiple medications that commonly includes a PI. Moreover, these patients often times require additional medications such as antibiotics and lipid lowering agents to control opportunistic infections and other diseases or conditions they may be afflicted with. Consequently, these patients can take an extraordinary number of medications in a variety of different dosage forms over the course of a given day.

Such treatment regimens are further complicated by the fact that some of the dosage forms (including some PI's) require refrigerated storage conditions to prevent degradation of the active ingredients. For subjects residing in economically challenged or developing countries where refrigerators are not as common in households, such storage conditions represent a particularly challenging dilemma.

It has also been observed that upon administration of a PI from gelatin capsules there is variability in the blood levels of the active ingredient from subject to subject and even within the same subject. That is, some patients receiving treatment can have very high or very low blood levels of the PI. In turn, this can lead to unwanted adverse events in those patients experiencing high blood levels of the drug or rendering the treatment less effective or ineffective in those patients experiencing low blood levels of the drug.

In order to increase the bioavailability of PI's it is recommended that patients take the gelatin capsule formulation following a meal to increase the overall bioavailability of the active ingredient. Bioavailability can further vary depending on fat content in each meal. Unfortunately, many patients do not always adhere to this routine due to the complexity of their treatment regimens or otherwise. Often patients will take the medication on an empty stomach that leads to low bioavailability of the drug, and perhaps ineffective treatment.

Therefore, it is desirable to have a PI dosage form that reduces or eliminates gastrointestinal adverse events. It is also desirable to have such a dosage form that can be loaded with more active ingredient to reduce the pill burden on patients. Furthermore, it is desirable to have a dosage form that provides little variability in the blood levels of the PI within a subject and throughout a patient population. Another desirable feature would be a dosage form that provides similar blood levels of a PI regardless of whether or not a patient takes the medication following a meal. Yet another desirable feature would be a dosage form that does not have to be refrigerated to prevent degradation of the PI.

SUMMARY OF THE INVENTION

Surprisingly, it has been discovered that by formulating an undissolved form of a PI (in particular lopinavir and a lopinavir/ritonavir combination) in a pharmaceutical dosage form, all of the aforementioned disadvantages associated with dosage forms containing a dissolved PI can be overcome. In particular, pharmaceutical dosage forms containing the undissolved PI reduce pill burdens on HIV patients, in large measure because the drug load in these formulations can be increased. Additionally, such formulations can be stored at room temperature and do not require refrigeration. Moreover, these formulations provide a more consistent blood level of the PI among patients taking such therapy which helps insure an effective therapeutic benefit and less adverse events. Further, these consistent blood levels can be achieved with the formulation provided herein without regard to whether or not the patient has eaten or what type of meal was eaten. It is believed that this is the first time that an undissolved form of lopinavir has been formulated in a solid dosage form. Given the advantages attendant to such formulation, this represents the next breakthrough in HIV therapy which will help ease the complicated treatment regimens currently prescribed for HIV patients.

IN THE DRAWINGS

Figure 2:
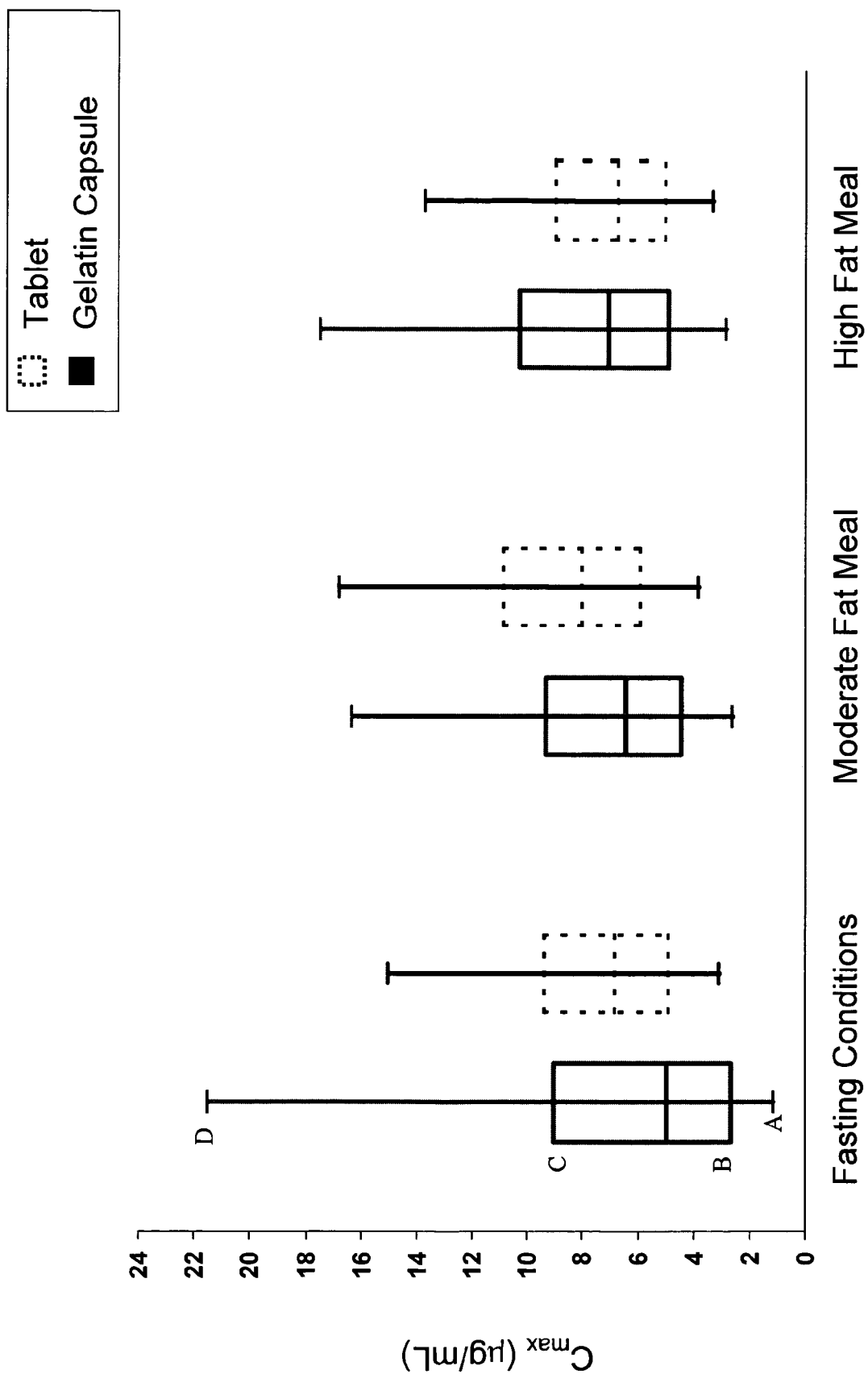

In the drawings,

FIG. 1 shows Box (lower and upper quartiles) and Whiskers ($5^{th}$ and $95^{th}$ percentiles) Plots for Lopinavir AUC Under Various Meal Conditions; and FIG. 2 shows Box (lower and upper quartiles) and Whiskers ($5^{th}$ and $95^{th}$ percentiles) Plots for Lopinavir Cmax Under Various Meal Conditions.

DETAILED DESCRIPTION OF THE INVENTION

Definitions

The term "AUC∞" is the area under the concentration time curve (AUC) extrapolated to infinity or the AUC to the last measured time point+(last measured concentration/elimination rate constant).

The term "Cmax" is defined as the observed maximum plasma concentration of an active ingredient.

"Pharmaceutically acceptable" as used herein means moieties or compounds that are, within the scope of sound medical judgment, suitable for use in contact with the tissues of humans and lower animals without undue toxicity, irritation, allergic response, and the like, and are commensurate with a reasonable benefit/risk ratio.

The term "weight percent" or "percent by weight" or "wt %" is defined as the weight of the individual component in the formulation divided by the total weight of all components of the formulation and then multiplied by 100. In some cases where a formulation has an outer coating, then weight of the coating can either be included or excluded in the total weight.

The phrase "fasting/fasted state or condition" generally is defined as 10 hours of abstinence from eating prior to dosing and 4 hours post-dosing, although those skilled in the art will recognize various other timings that would also qualify as a fasting or fasted state.

The phrase "moderate-fat meal condition" is defined as receiving a meal that is approximately 500-600 KCal wherein 20-30% of the calories are from fat served approximately 30 minutes prior to dosing.

The phrase "high-fat meal condition" is defined as receiving a meal that is approximately 1000 Kcal wherein 50-55% of the calories are from fat served approximately 30 minutes prior to dosing and is used herein to refer to a "fed state" although those skilled in the art will recognize various meal conditions that would also qualify as a fed state.

The term "solid solution" is defined as a system in a solid state wherein the drug is molecularly dispersed throughout a matrix such that the system is chemically and physically uniform or homogenous throughout.

The term "solid dispersion" is defined as a system having small particles, typically of less than 400 μm in size, more typically less than 100 μm in size, and most typically less than 10 μm in size, of one phase dispersed in another phase (the carrier phase).

Suitable PI's for use in accordance with the present invention include but are not limited to (2S,3S,5S)-5-(N-(N-((N-methyl-N-((2-isopropyl-4-thiazolyl)-methyl)amino)carbonyl)-L-valinyl)amino-2-(N-((5-thiazolyl)methoxy-carbonyl)-amino)-amino-1,6-diphenyl-3hydroxyhexane (ritonavir); (2S,3S,5S)-2-(2,6-Dimethylphenoxyacetyl) amino-3-hydroxy-5-[2S-(1-tetrahydro-pyrimid-2-onyl)-3-methylbutanoyl]-amino-1,6-diphenylhexane (ABT-378; lopinavir); N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide (indinavir); N-tert-butyl-decahydro-2-[2(R)-hydroxy-4-phenyl-3(S)-[[N-(2-quinolylcarbonyl)-L-asparaginyl]amino]butyl]-(4aS, 8aS)-isoquinoline-3(S)-carboxamide (saquinavir); 5(S)-Boc-amino-4(S)-hydroxy-6-phenyl-2(R) phenylmethylhexanoyl-(L)-Val-(L)-Phe-morpholin-4-ylamide; 1-Naphthoxyacetyl-beta-methylthio-Ala-(2S,3S)3-amino-2-hydroxy-4-butanoyl-1,3-thiazolidine-4t-butylamide; 5-isoquinolinoxyacetyl-beta-methylthio-Ala-(2S,3S)-3amino-2-hydroxy-4-butanoyl-1,3-thiazolidine-4-tbutylamide; [1S-[1R-(R-),2S*])-N$^1$ [3-[[[(1,1-dimethylethyl)amino]carbonyl](2-methylpropyl)amino]-2hydroxy-1-(phenylmethyl)propyl]-2-[(2-quinolinylcarbonyl)amino]-butanediamide; amprenavir (VX-478); DMP-323; DMP-450; AG1343 (nelfinavir); atazanavir (BMS 232,632); tipranavir; palinavir; TMC-114; RO033-4649; fosamprenavir (GW433908); P-1946; BMS 186,318; SC-55389a; BILA 1096 BS; and U-140690, or any combinations thereof, whether used for PI activity or otherwise, such as with the case of ritonavir that can sometimes be employed as a cytochrome P450 monooxygenase inhibitor (variously referred to as a "pK booster). Preferred PIs are lopinavir and ritonavir alone, or in combination.

Generally, dosage forms of the present invention will comprise a therapeutically effective amount of at least one PI. The specific therapeutically effective dose level for any particular patient will depend upon a variety of factors including the severity of the disorder; the activity of the specific compound employed; the specific composition employed; the age, body weight, general health, sex and diet of the patient; the time of administration, and rate of excretion of the specific compound employed; the duration of the treatment; drugs used in combination or coincidental with the specific compound employed; and other factors known to those of ordinary skill in the medical arts. For example, it is well within the skill of the art to start doses of the compound at levels lower than required to achieve the desired therapeutic effect and to gradually increase the dosage until the desired effect is achieved. Typically, however, a pharmaceutical dosage form of the present invention will comprise from about 5 to about 30% by weight of the total dosage form, preferably from about 10 to about 25% by weight of the total dosage form, of an HIV protease inhibitor or a combination of HIV protease inhibitors. Preferably, the dosage form will contain between about 10 mg to about 1500 mg of a PI. Most preferably, the dosage form will comprise lopinavir and ritonavir in a ratio of about 4:1 respectively. The preferred dose of lopinavir and ritonavir is 400 mg and 100 mg respectively which can be divided evenly between multiple dosage forms, preferably two. It will be understood that multiple doses, typically two, can be given in a given day.

Pharmaceutical dosage forms provided herein generally will comprise an "undissolved" PI. In contradistinction to existing gelatin capsules filled with a PI dissolved in a solvent, undissolved PI's as used herein means that the PI is in a solid form and not dissolved in a liquid carrier in its final dosage form. Solid forms of a PI may include, for example, crystalline, micronized crystalline, crystalline nanoparticulates, amorphous, micronized amorphous, amorphous nanoparticulates, or preferably amorphous solid forms of a PI.

Many pharmaceutical dosage forms are acceptable for use in accordance with the present invention; the choice of which is well within the skill of a person of ordinary skill in this art based upon the properties of the dosage forms provided herein. For example, orally administered solid dosage forms include but are not limited to capsules, dragees, granules, pills, powders, and tablets. Excipients commonly used to formulate such dosage forms include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, preservatives, propellants, releasing agents, sterilizing agents, sweeteners, solubilizers, and mixtures thereof. Excipients for orally administered compounds in solid dosage forms include agar, alginic acid, aluminum hydroxide, benzyl benzoate, 1,3-butylene glycol, castor oil, cellulose, cellulose acetate, cocoa butter, corn starch, corn oil, cottonseed oil, ethanol, ethyl acetate, ethyl carbonate, ethyl cellulose, ethyl laureate, ethyl oleate, gelatin, germ oil, glucose, glycerol, groundnut oil, isopropanol, isotonic saline, lactose, magnesium hydroxide, magnesium stearate, malt, olive oil, peanut oil, potassium phosphate salts, potato starch, propylene glycol, talc, tragacanth, water, safflower oil, sesame oil, sodium carboxymethyl cellulose, sodium lauryl sulfate, sodium phosphate salts, soybean oil, sucrose, tetrahydrofurfuryl alcohol, and mixtures thereof.

A preferred dosage form, will generally comprise at least one HIV protease inhibitor in a therapeutically effective amount, at least one pharmaceutically acceptable water-soluble polymer and at least one pharmaceutically acceptable surfactant.

More preferably, a solid solution or solid dispersion can be formed into one of the above pharmaceutical dosage forms. Such solutions or dispersions can be manufactured with suitable pharmaceutically acceptable water-soluble polymers including but not limited to water-soluble polymers having a Tg of at least about 50° C., preferably at least about 60° C., most preferred from about 80° C. to about 180° C. Methods for determining Tg values of the organic polymers are described in "Introduction to Physical Polymer Science", 2nd Edition by L. H. Sperling, published by John Wiley & Sons, Inc., 1992. The Tg value can be calculated as the weighted sum of the Tg values for homopolymers derived from each of the individual monomers, i.e., that make up the polymer: $Tg=\Sigma W_i X_i$ where W is the weight percent of monomer i in the organic polymer, and X is the Tg value for the homopolymer derived from monomer i. Tg values for the homopolymers may be taken from "Polymer Handbook", 2nd Edition by J. Brandrup and E. H. Immergut, Editors, published by John Wiley & Sons, Inc., 1975.

Water-soluble polymers having a Tg as defined above allow for the preparation of solid solutions or solid dispersions that are mechanically stable and, within ordinary temperature ranges, sufficiently temperature stable so that the solid solutions or solid dispersions may be used as dosage forms without further processing or be compacted to tablets with only a small amount of tableting aids.

The water-soluble polymer comprised in the preferred dosage form is a polymer that preferably has an apparent viscosity, when dissolved at 20° C. in an aqueous solution at 2% (w/v), of about 1 to about 5000 mPa·s., and more preferably of about 1 to about 700 mPa·s, and most preferred of about 5 to about 100 mPa·s.

Water-soluble polymers suitable for use in the preferred dosage form of the present invention include but are not limited to homopolymers and copolymers of N-vinyl lactams, especially homopolymers and copolymers of N-vinyl pyrrolidone, e.g. polyvinylpyrrolidone (PVP), copolymers of N-vinyl pyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate; high molecular polyalkylene oxides such as polyethylene oxide and polypropylene oxide and copolymers of ethylene oxide and propylene oxide, polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, oligo- and polysaccharides such as carrageenans, galactomannans and xanthan gum, or mixtures of one or more thereof.

Of these, homopolymers or copolymers of N-vinyl pyrrolidone, in particular a copolymer of N-vinyl pyrrolidone and vinyl acetate, are preferred. A particularly preferred polymer is a copolymer of about 60% by weight of the copolymer, N-vinyl pyrrolidone and about 40% by weight of the copolymer, vinyl acetate.

According to the preferred dosage form of the present invention, the pharmaceutical dosage form comprises from about 50 to about 85% by weight of the total dosage form, preferably from about 60 to about 80% by weight of the total dosage form, of a water-soluble polymer or any combination of such polymers.

The term "pharmaceutically acceptable surfactant" as used herein refers to a pharmaceutically acceptable non-ionic surfactant. In one embodiment, the present invention provides a dosage form comprising at least one surfactant having an hydrophilic lipophilic balance (HLB) value of from about 4 to about 10, preferably from about 7 to about 9. The HLB system (Fiedler, H. B., Encylopedia of Excipients, $5^{th}$ ed., Aulendorf: ECV-Editio-Cantor-Verlag (2002)) attributes numeric values to surfactants, with lipophilic substances receiving lower HLB values and hydrophilic substances receiving higher HLB values.

Surfactants having an HLB value of from about 4 to about 10 suitable for use in the present invention include but are not limited to polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (Lauroglycol®); sucrose fatty acid esters, e.g. sucrose monostearate, sucrose distearate, sucrose monolaurate, sucrose dilaurate; or sorbitan fatty acid mono esters such as sorbitan mono laurate (Span® 20), sorbitan monooleate, sorbitan monopalmitate (Span® 40), or sorbitan stearate, or mixtures of one or more thereof.

The sorbitan mono fatty acid esters are preferred, with sorbitan mono laurate and sorbitan monopalmitate being particularly preferred.

A preferred dosage form of the present invention comprises from about 2 to about 20% by weight of the total dosage form, preferably from about 3 to about 15% by weight of the total dosage form, of the surfactant or combination of surfactants.

Besides the surfactant having an HLB value of from about 4 to about 10, the preferred dosage form may comprise additional pharmaceutically acceptable surfactants such as polyoxyethylene castor oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40) or polyethylenglycol 60 hydrogenated castor oil (Cremophor® RH 60); or block copolymers of ethylene oxide and propylene oxide, also known as polyoxyethylene polyoxypropylene block copolymers or polyoxyethylene polypropyleneglycol, such as Poloxamer® 124, Poloxamer® 188, Poloxamer® 237, Poloxamer® 388, Poloxamer® 407 (BASF Wyandotte Corp.); or a mono fatty acid ester of polyoxyethylene (2) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), polyoxyethylene (20) sorbitan monolaurate (Tween® 20).

Where such additional surfactants are used, the surfactant having an HLB value of from about 4 to about 10 generally accounts for at least about 50% by weight, preferably at least about 60% by weight, of the total amount of surfactant used.

The dosage form of the present invention can include additional excipients or additives such as, for example, flow regulators, lubricants, bulking agents (fillers) and disintegrants. Such additional excipients may comprise from about 0 to about 15% by weight of the total dosage form.

The preferred solid dispersion or solid solution based dosage form of the present invention can be produced by preparing a solid solution or solid dispersion of the HIV protease inhibitor, or the combination of HIV protease inhibitors, in a matrix of a water-soluble polymer and a surfactant, and then shaping into the required tablet form. Alternatively, the solid solution or solid dispersion product can be subdivided to granules, e.g. by grinding or milling, and the granules may subsequently be compacted to tablets.

Various techniques exist for preparing solid solutions or solid dispersions including melt-extrusion, spray-drying and solution-evaporation with melt-extrusion being preferred.

The melt-extrusion process comprises the steps of preparing a homogeneous melt of the HIV protease inhibitor or the combination of HIV protease inhibitors, the water-soluble polymer and the surfactant, and cooling the melt until it solidifies. "Melting" means a transition into a liquid or rubbery state in which it is possible for one component to get embedded homogeneously in the other. Typically, one component will melt and the other components will dissolve in the melt thus forming a solution. Melting usually involves heating above the softening point of the water-soluble polymer. The preparation of the melt can take place in a variety of ways. The mixing of the components can take place before, during or after the formation of the melt. For example, the components can be mixed first and then melted or be simultaneously mixed and melted. Usually, the melt is homogenized in order to disperse the active ingredients efficiently. Also, it may be convenient first to melt the water-soluble polymer and then to mix in and homogenize the active ingredients.

Usually, the melt temperature is in the range of about 70 to about 250° C., preferably from about 80 to about 180° C., most preferred from about 100 to about 140° C.

The active ingredients can be employed as such or as a solution or dispersion in a suitable solvent such as alcohols, aliphatic hydrocarbons or esters. Another solvent which can be used is liquid carbon dioxide. The solvent is removed, e.g. evaporated, upon preparation of the melt.

Various additives may be included in the melt, for example flow regulators such as colloidal silica; lubricants, fillers, disintegrants, plasticizers, stabilizers such as antioxidants, light stabilizers, radical scavengers, stabilizers against microbial attack.

The melting and/or mixing takes place in an apparatus customary for this purpose. Particularly suitable ones are extruders or kneaders. Suitable extruders include single screw extruders, intermeshing screw extruders or else multi-screw extruders, preferably twin screw extruders, which can be corotating or counterrotating and, optionally, be equipped with kneading disks. It will be appreciated that the working temperatures will also be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt ranges from pasty to viscous. Shaping of the extrudate conveniently is carried out by a calender with two counter-rotating rollers with mutually matching depressions on their surface. A broad range of tablet forms can be attained by using rollers with different forms of depressions. Alternatively, the extrudate is cut into pieces, either before (hot-cut) or after solidification (cold-cut).

Optionally, the resulting solid solution or solid dispersion product is milled or ground to granules. The granules may then be compacted. Compacting means a process whereby a powder mass comprising the granules is densified under high pressure in order to obtain a compact with low porosity, e.g. a tablet. Compression of the powder mass is usually done in a tablet press, more specifically in a steel die between two moving punches. Where a solid dosage form of the invention comprises a combination of more than one HIV protease inhibitor (or a combination of an HIV protease inhibitor with one or more other active ingredients) it is of course possible to separately prepare solid solution or solid dispersion products of the individual active ingredients and to blend the milled or ground products before compacting.

At least one additive selected from flow regulators, disintegrants, bulking agents (fillers) and lubricants is preferably used in compacting the granules. Disintegrants promote a rapid disintegration of the compact in the stomach and keeps the granules which are liberated separate from one another. Suitable disintegrants are crosslinked polymers such as crosslinked polyvinyl pyrrolidone and crosslinked sodium carboxymethylcellulose. Suitable bulking agents (also referred to as "fillers") are selected from lactose, calcium hydrogenphosphate, microcrystalline cellulose (Avicell®), silicates, in particular silicium dioxide, magnesium oxide, talc, potato or corn starch, isomalt, polyvinyl alcohol.

Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, and the like.

Various other additives may be used, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack.

Dosage forms according to the invention may be provided as dosage forms consisting of several layers, for example laminated or multilayer tablets. They can be in open or closed form. "Closed dosage forms" are those in which one layer is completely surrounded by at least one other layer. Multilayer forms have the advantage that two active ingredients which are incompatible with one another can be processed, or that the release characteristics of the active ingredient(s) can be controlled. For example, it is possible to provide an initial dose by including an active ingredient in one of the outer layers, and a maintenance dose by including the active ingredient in the inner layer(s). Multilayer tablets types may be produced by compressing two or more layers of granules. Alternatively, multilayer dosage forms may be produced by a process known as "coextrusion". In essence, the process comprises preparation of at least two different melt compositions as explained above, and passing these molten compositions into a joint coextrusion die. The shape of the coextrusion die depends on the required drug form. For example, dies with a plain die gap, called slot dies, and dies with an annular slit are suitable.

In order to facilitate the intake of such a dosage form by a mammal, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. If desired, the film-coat may be an enteric coat. The film-coat usually includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. a Tween® type, and optionally a pigment, e.g.

titanium dioxide or iron oxides. The film-coating may also comprise talc as anti-adhesive. The film coat usually accounts for less than about 5% by weight of the dosage form.

The benefits provided by the present invention are presently believed to be attributable to the pharmacokinetic (pK) properties of the dosage form. Pharmacokinetic properties are generally understood to mean the manner and extent to which a drug is absorbed. Common pK parameters include AUC (or "area under the curve"), which typically refers to the amount of drug that is measurable in blood or blood products of a person taking the drug over time. AUC is variously referred to as a patients exposure to a drug. Cmax is another pK term which refers to the maximum blood (or blood product) level over the course of a given regimen of a drug. Drug regimens for which pK parameters are measured include "clinical studies." Some clinical studies are performed in a finite population of healthy volunteer patients and are designed to determine the pK parameters of a drug (such as those mentioned above), and not to treat a patient. Each patient is thus called a member of the study population. While such clinical studies are carefully controlled and monitored, pK parameters can vary between clinical studies in large measure because different clinical studies are performed on different populations of patients. Although variances exist between clinical studies, those skilled in the art readily recognize that once a particular set of pK parameters is generally known, it is a matter of routine to formulate a drug to achieve a similar set of pK parameters.

As previously mentioned, the present invention provides a dosage form that can be taken without regard to whether a patient has eaten, sometimes referred to as "without regard to meals", "can be taken with or without food", "no food effect" or similar phrases. In particular, the Cmax of the drug and AUC of the drug is similar in patients that have eaten ("fed state") as compared to patients that have not eaten ("fasted state"). Hence, the dosage form provided herein advantageously can be taken at any time regardless of whether or not patients have recently eaten.

Notwithstanding the previous definition, there is no completely standard definitions for fed and fasted states. Generally, however, a fasted state refers to the fact that a patient has not eaten for a given amount of time before taking a dose of medication, as well as not eating for a given amount of time after taking the dosage form. These time periods before and after dosing are a matter of choice, and can range between, for example 2 hours to 24 hours. A fed state generally refers to the fact that a patient has eaten within a given time period of taking a particular medication. This time period is variable but may constitute, for example, a meal just before, during, or just after taking the medication, typically a meal is eaten within about an hour of dosing. The quantity of food eaten that will qualify as a fed state is also variable but generally can comprise between about 500 to about 1500 Kcal of food.

The dosage forms provided herein will have substantially the same Cmax and AUC∞ values in patients in a fasted state as well as in a fed state, regardless of the dose given. In particular, the mean of the individual patient ratios in a patient population for either the Cmax or AUC∞ in the fed state to fasted state will be in the range of about 0.7 to about 1.43; more preferably between about 0.75 and about 1.35; and most preferably between about 0.8 and about 1.25. Thus for example, in study population of 30 individuals each patient is given a dose of drug in a fed state and, after an appropriate time period, a dose of the drug in a fasted state. The AUC∞ and Cmax for both meal conditions are calculated for each patient. The AUC∞ value for the fed state is then divided by the AUC∞ for the fasted state for each patient. The individual patient values are then added together and then divided by the number of patients completing the study to arrive at a mean AUC∞ value for all patients completing the study. The mean Cmax value is calculated in a similar manner. If the mean value of the fed to fasted ratio for all patients' Cmax or AUC∞ values in a given study is within 0.7 to 1.43, for example, then the dosage form provided to the patients would be considered to capable of administration without regard to whether or not the patient was in a fed or fasted state.

As also previously mentioned, the dosage forms provided herein have less variability than other gelatin capsule based formulations containing a dissolved form of the drug or drugs. This lack of variability is evidenced in FIG. 1 and FIG. 2 which compare AUC∞ and Cmax data of an embodiment of the present invention and the data from a marketed gelatin capsule containing a dissolved PI. As shown by the Figures, the AUC∞ and Cmax data associated with an embodiment of the present invention shows less variation. In particular, the graphs are a "box and whiskers" plot of the data comparing the two formulations wherein the bottom of any given "whisker" (labeled A in the first box and whisker plot of FIG. 1) is called the "5th percentile", meaning that 5% of the patients in the study fell below the designated AUC∞ or Cmax value for the particular whisker. The top of the whisker (labeled D in first box and whisker plot of FIG. 1) represents the "$95^{th}$ percentile", meaning that 5% of the patients in the study had a AUC∞ or Cmax value above the value designated by the top of any particular whisker. Similarly, the bottom of any particular box (labeled B in first box and whisker plot of FIG. 1) represents the $25^{th}$ percentile and the top of any particular box (labeled C in first box and whisker plot of FIG. 1) represent the $75^{th}$ percentile. The line running through any particular box is the $50^{th}$ percentile or median of any particular study population.

As seen by the Figures, the data generally demonstrates that the variability associated with the embodiment of the present invention is less than that associated with the existing gelatin capsule formulation. Looking at the dosage forms given under fasting conditions of FIG. 1 (for example), the difference between $95^{th}$ percentile and $5^{th}$ percentile of the gelatin capsule is greater than the difference between $95^{th}$ percentile and $5^{th}$ percentile of the embodiment of the present invention. This translates into the fact that a greater portion of the study population is getting a therapeutic benefit from the PI without experiencing adverse events do to overexposure of the drug. For purposes of, for example, reducing side effects and achieving therapeutic levels, it is generally preferred that the difference between the $95^{th}$ percentile of AUC∞ and $5^{th}$ percentile of AUC∞ of any given study population taking a dosage form as provided herein (regardless of whether the population is fed or fasted) is less than about 180, more preferably less than about 175, even more preferably less than about 165, and most preferably less than about 160. Under fasting conditions, it is preferable that the difference between the $95^{th}$ percentile of AUC∞ and $5^{th}$ percentile of AUC∞ of any given study population taking a dosage form as provided herein is less than about 170, more preferably less than about 160, and most preferably less than about 150. Under fed conditions, it is preferable that the difference between the $95^{th}$ percentile of AUC∞ and $5^{th}$ percentile of AUC∞ of any given study population taking a dosage form as provided herein is less than about 130, more preferably less than about 120, and most preferably less than about 110.

Similarly to the differences between the $95^{th}$ and $5^{th}$ percentiles provided above, the difference between the $75^{th}$ percentile and $25^{th}$ percentile of the AUC data in FIG. 1 is also very important in demonstrating the lack of variability in dosage forms of the present invention. It is generally preferred that the difference between the 75$^{th}$ percentile of AUC∞ and 25$^{th}$ percentile of AUC∞ of any given study population taking a dosage form as provided herein (regardless of whether the population is fed or fasted) is less than about 60, more preferably less than about 55, even more preferably less than about 50. Under fasting conditions, it is preferable that the difference between the 75$^{th}$ percentile of AUC∞ and 25$^{th}$ percentile of AUC∞ of any given study population taking a dosage form as provided herein is less than about 65, more preferably less than about 60, and most preferably less than about 55. Under fed conditions, it is preferable that the difference between the 75$^{th}$ percentile of AUC∞ and 25$^{th}$ percentile of AUC∞ of any given study population taking a dosage form as provided herein is less than about 60, more preferably less than about 50, and most preferably less than about 40.

In terms of ranges of AUC∞ values, it is preferred that under fasted conditions the 5$^{th}$ percentile to the 95$^{th}$ percentile of AUC∞ of any given study population taking a dosage form as provided herein ranges between about 33 µg•h/mL and about 175 µg•h/mL; and the 25$^{th}$ percentile to the 75$^{th}$ percentile of AUC∞ of any given study population taking a dosage form as provided ranges between about 54 µg•h/mL and about 107 µg•h/mL. Under fed conditions it is preferred that the 5$^{th}$ percentile to the 95$^{th}$ percentile of AUC∞ of any given study population taking a dosage form as provided herein ranges between about 57 µg•h/mL and about 142 µg•h/mL; and the 25$^{th}$ percentile to the 75$^{th}$ percentile of AUC∞ of any given study population taking a dosage form as provided herein ranges between about 75 µg•h/mL and about 109 µg•h/mL. It is also preferred that the 5$^{th}$ percentile of the AUC∞ of any given study population taking a dosage form as provided herein greater than about 30 µg•h/mL under fasted conditions, and greater than about 50 µg•h/mL under fed conditions. Finally with respect to AUC∞, it is preferred that under fasting conditions the mean AUC∞ is between about 60 µg•h/mL and about 95 µg•h/mL. for any given study population taking a dosage form provided.

Similarly to the AUC parameters associated with FIG. 1, the Cmax parameters shown in FIG. 2 also demonstrates lack of variability associated with dosage forms provided herein. For example, looking at the box and whiskers plot of FIG. 2 for patients under fasting conditions taking a dose of PI formulated according to the present invention, it is preferred that difference between the 95$^{th}$ percentile and the 5$^{th}$ percentile is less than about 15, more preferably less than about 13, and most preferably less than about 11. Under fasted conditions it is also preferable that the 5$^{th}$ percentile of Cmax of a given study population taking a dose of active ingredient formulated according to the present invention is greater that about 2.5 µg/mL. Turning to the box and whiskers plot of FIG. 2 for fed conditions taking a dosage form of the present invention, it is preferred that difference between the 95$^{th}$ percentile and the 5$^{th}$ percentile is less than about 12, more preferably less than about 11.

With respect to the description of the figures provided above, it should be pointed out that when a patient is referred to as taking a dosage form of the present invention, they received a dose of a PI in multiple dosage forms. Specifically, the so called dosage form contained 400 mg of lopinavir and 100 mg of ritonovir evenly divided between two dosage forms. Lopinavir was the only drug measured in these studies due to the fact that ritonavir is supplied not for its action as a PI but as a pharmacokinetic enhancer or booster (ritonavir inhibits the metabolism of lopinavir). Further, it will be understood that the when ritonavir is employed it can be separately dosed instead of part of a combination dosage form. Moreover, it will be understood that the values given can vary due to, for example, changes in meal timings and quantities, as well as the constitution of the study population. It is well known that study populations from different nationalities may have different drug metabolism rates. Accordingly, in cases where study data is taken from such populations, the data may have to be normalized as is well known in the art. Moreover, in cases where an increase in the dose or a decrease in the dose of lopinovir, for example, is provided to a study population, the data resulting from such dosing may require normalization using appropriate modeling as is well known in the art. Last, with respect to the above discussion concerning the figures, a "High Fat Meal" as described in the figures is considered to be a fed state.

In addition to providing methods of treating a human patient afflicted with HIV/AIDs, the present invention provides methods of reducing the side effects associated with HIV therapy, methods of increasing the bioavailability of a PI, methods of decreasing the pill burden of an HIV/AIDs patient, methods of decreasing the variability of blood levels of a PI in a patient taking PI therapy, and methods of providing a PI to a patient taking PI therapy. All of these methods comprise the step of providing a pharmaceutical dosage form comprising a therapeutically effective amount of an undissolved form of a PI to a patient. Preferably, the PI is (2S,3S, 5S)-2-(2,6-Dimethylphenoxyacetyl)amino-3-hydroxy-5-[2S-(1-tetrahydro-pyrimid-2-onyl)-3-methylbutanoyl]-amino-1,6-diphenylhexane (ABT-378; lopinavir). More preferably, the dosage form will comprise (2S,3S,5S)-5-(N-(N-((N-methyl-N-((2-isopropyl-4-thiazolyl)methyl)amino) carbonyl)-L-valinyl)amino-2-(N-((5-thiazolyl)-methoxy-carbonyl)-amino)-amino-1,6-diphenyl-3hydroxyhexane (ritonavir).

EXAMPLES

The following examples are provided to further understand and illustrate the present invention and not to limit the spirit and scope of the present invention as it is defined in the appended claims.

Example 1

| Component | Weight % | Weight % | Weight % |
|---|---|---|---|
| Ritonavir | 18-22.5 | 4.17 | 4.17 |
| Lopinavir | in total | 16.67 | 16.67 |
| Copovidone (N-vinyl pyrrolidone/vinyl acetate copolymer 60:40) | 65-75 | 71.16 | 70.12 |
| Span 20 (Sorbitan monolaurate) | 4-10 | 7.0 | 5.02 |
| Cremophor RH40 (polyoxyethyleneglycerol oxystearate) | 0-10 | — | 3.02 |
| Colloidal silica | 0-3 | 1.0 | 1.0 |

Copovidone (N-vinyl pyrrolidone/vinyl acetate copolymer 60:40) was mixed with ritonavir (4.17 parts by weight), lopinavir (16.67 parts by weight) and colloidal silica (1.0 part by weight). The powdery mixture was then fed into a twin-screw extruder (screw diameter 18 mm) at a rate of 2.0 kg/h and a melt temperature of 133° C. The clear, fully transparent melt was fed to a calender with two counter-rotating rollers having mutually matching cavities on their surfaces. Tablets of 1080 mg were thus obtained. DSC and WAXS analysis did not reveal any evidence of crystalline drug material in the formulation.

The bioavailability of the formulation was assessed using beagle dogs (mixed sexes, weighing approximately 10 kg) which received a balanced diet with 27% fat and were permitted water ad libitum. Each dog received a 100 µg/kg subcutaneous dose of histamine approximately 30 minutes prior to dosing. A single dose corresponding to about 200 mg lopinavir, about 50 mg ritonavir, or about 200 mg lopinavir and about 50 mg ritonavir, respectively, was administered to each dog. The dose was followed by approximately 10 milliliters of water. Blood samples were obtained from each animal prior to dosing and 0.25, 0.5, 1.0, 1.5, 2, 3, 4, 6, 8, 10, 12 and 24 hours after drug administration. The plasma was separated from the red cells by centrifugation and frozen (−30° C.) until analysis. Concentrations of HIV protease inhibitors were determined by reverse phase HPLC with low wavelength UV detection following liquid-liquid extraction of the plasma samples. The area under the curve (AUC) was calculated by the trapezoidal method over the time course of the study. Each dosage form was evaluated in a group containing 8 dogs; the values reported are averages for each group of dogs.

The dose-adjusted AUC in dogs was 0.52 µg.h/ml/100 mg for ritonavir and 4.54 µg.h/ml/100 mg for lopinavir. This example shows that solid solutions or solid dispersions of HIV protease inhibitors without added surfactant yield a very poor bioavailability.

Example 2

| Component | Weight % | Weight % |
|---|---|---|
| Ritonavir | 18-22.5 | 20.8 |
| Lopinavir | — | — |
| Copovidone (N-vinyl pyrrolidone/vinyl acetate copolymer 60:40) | 60-75 | 63.15 |
| Span 20 (Sorbitan monolaurate) | 5-15 in total | — |
| Cremophor RH40 (polyoxyethyleneglycerol oxystearate) | | 10.00 |
| PEG 6000 | 0-8 | 5.00 |
| Colloidal silica | 0-3 | 1.04 |

The above composition is processed by melt extrusion. The resulting extrudate can be used as such or milled and compressed into tablets, preferably by the use of suitable tabletting aids such as sodium stearyl fumarate, colloidal silica, lactose, isomalt, calcium silicate, and magnesium stearate, cellulose or calcium hydrogenphosphate.

Example 3

| Component | Weight % |
|---|---|
| Ritonavir | 4.16 |
| Lopinavir | 16.67 |
| Copovidone (N-vinyl pyrrolidone/vinyl acetate copolymer 60:40) | 78.17 |
| Colloidal silica | 1.0 |

Copovidone (N-vinyl pyrrolidone/vinyl acetate copolymer 60:40; 78.17 parts by weight) was mixed with ritonavir (4.16 parts by weight), lopinavir (16.67 parts by weight) and colloidal silica (1.0 part by weight). The powdery mixture was then fed into a twin-screw extruder (screw diameter 18 mm) at a rate of 2.0 kg/h and a melt temperature of 133° C. The clear, fully transparent melt was fed to a calender with two counter-rotating rollers having mutually matching cavities on their surfaces. Tablets of 1080 mg were thus obtained. DSC and WAXS analysis did not reveal any evidence of crystalline drug material in the formulation.

Example 4

| Component | Weight % |
|---|---|
| Ritonavir | 4.17 |
| Lopinavir | 16.67 |
| Copovidone | 68.17 |
| Cremophor RH40 | 10.00 |
| colloidal silica | 1.0 |
| lactose monohydrate | 6.0 |
| crosslinked PVP | 6.0 |
| colloidal silica | 1.0 |
| magnesium stearate | 0.51 |

Copovidone (N-vinyl pyrrolidone/vinyl acetate copolymer 60:40; 68.17 parts by weight) was blended with Cremophor RH40 (polyoxyethyleneglycerol oxystearate; 10.00 parts by weight) in a Diosna high-shear mixer. The resulting granules were mixed with ritonavir (4.17 parts by weight), lopinavir (16.67 parts by weight) and colloidal silica (1.00 parts by weight). The powdery mixture was then fed into a Leistritz Micro 18 twin-screw extruder at a rate of 2.3 kg/h and a melt temperature of 126° C. The extrudate was cut into pieces and allowed to solidify. The extruded pieces were milled using a high impact universal mill. The milled material (86.49 parts by weight) was blended in a bin blender with lactose monohydrate (6.00 parts by weight), crosslinked PVP (6.00 parts by weight), colloidal silica (1.00 part by weight) and magnesium stearate (0.51 parts by weight). The powdery blend was compressed to tablets of 1378.0 mg on a Fette E 1 single punch tablet press. The tablets were then film-coated in a coating pan by spraying an aqueous dispersion for film coating (Opadry, available from Colorcon) at a temperature of 60° C.

The bioavailability of the formulation was assessed using beagle dogs as in Example 1. The dose-adjusted AUC in dogs was 0.60 µg.h/ml/100 mg for ritonavir and 7.43 µg.h/ml/100 mg for lopinavir. This example shows that inclusion of a surfactant into solid solutions or solid dispersions of HIV protease inhibitors improves the bioavailability attained.

Example 5

| Component | Weight (mg) |
|---|---|
| Ritonavir | 50 |
| Lopinavir | 200 |
| Copovidone | 853.8 |
| Span 20 | 83.9 |
| colloidal silica | 12 |

Copovidone (N-vinyl pyrrolidone/vinyl acetate copolymer 60:40; 853.8 parts by weight) was blended with Span 20 (Sorbitan monolaurate; 83.9 parts by weight) in a Diosna high-shear mixer. The resulting granules were mixed with ritonavir (50 parts by weight), lopinavir (200 parts by weight) and colloidal silica (12 parts by weight). The powdery mixture was then fed into a twin-screw extruder (screw diameter 18 mm) at a rate of 2.1 kg/h and a melt temperature of 119° C. The extrudate was fed to a calender with two counter-rotating rollers having mutually matching cavities on their surfaces. Tablets of 1120 mg were thus obtained.

The bioavailability of the formulation was assessed using beagle dogs as in Example 1. The dose-adjusted AUC in dogs was 10.88 µg.h/ml/100 mg for ritonavir and 51.2 µg.h/ml/100 mg for lopinavir. This example shows that inclusion of a surfactant having an HLB of 4 to 10 into solid solutions or solid dispersions of HIV protease inhibitors markedly improves the bioavailability attained.

Example 6

Example 5 was repeated, however, the extrudate was cut into pieces and allowed to solidify. The extruded pieces were milled to a particle size of about 250 µm, using a high impact universal mill. The milled material was blended in a bin blender with sodium stearyl fumarate (12.3 parts by weight) and colloidal silica (8.0 parts by weight) for 20 min. The powdery blend was compressed on a rotary tablet machine with 3 punches (6500 tablets/h). The tablets were then film-coated in a coating pan by spraying an aqueous dispersion for film coating (Opadry, available from Colorcon) at a temperature of 60° C.

The bioavailability of the formulation was assessed using beagle dogs as in Example 1. The dose-adjusted AUC in dogs was 14.24 µg.h/ml/100 mg for ritonavir and 52.2 µg.h/ml/100 mg for lopinavir.

Example 7

| Component | Weight (mg) |
| --- | --- |
| Ritonavir | 50 |
| Lopinavir | 200 |
| Copovidone | 841.3 |
| Span 20 | 60.2 |
| Cremophor RH40 | 36.2 |
| colloidal silica | 12 |

Copovidone (N-vinyl pyrrolidone/vinyl acetate copolymer 60:40; 841.3 parts by weight) was blended with Cremophor RH40 (polyoxyethyleneglycerol oxystearate; 36.2 parts by weight), Span 20 (Sorbitan monolaurate; 60.2 parts by weight) in a Diosna high-shear mixer. The resulting granules were mixed with ritonavir (50 parts by weight), lopinavir (200 parts by weight) and colloidal silica (12 parts by weight). The powdery mixture was then fed into a twin-screw extruder (screw diameter 18 mm) at a rate of 2.1 kg/h and a melt temperature of 114° C. The extrudate was fed to a calender with two counter-rotating rollers having mutually matching cavities on their surfaces. Tablets of 1120 mg were thus obtained.

The bioavailability of the formulation was assessed using beagle dogs as in Example 1. The dose-adjusted AUC in dogs was 10.96 µg.h/ml/100 mg for ritonavir and 46.5 µg.h/ml/100 mg for lopinavir. This example shows that a combination of a surfactant having an HLB of 4 to 10 and a further surfactant can successfully be used.

Example 8

Example 7 was repeated, however, the extrudate was cut into pieces and allowed to solidify. The extruded pieces were milled to a particle size of about 250 µm, using a high impact universal mill. The milled material was blended in a bin blender with sodium stearylfumarate (13.9 parts by weight), colloidal silica (7.0 parts by weight), isomalt DC100 (159.4 parts by weight) and calcium silicate (7.0 parts by weight) for 20 min. The blend was compressed and then film-coated in a coating pan by spraying an aqueous dispersion for film coating (Opadry, available from Colorcon) at a temperature of 60° C.

The bioavailability of the formulation was assessed using beagle dogs as in Example 1. The dose-adjusted AUC in dogs was 10.38 µg.h/ml/100 mg for ritonavir and 42.7 µg.h/ml/100 mg for lopinavir.

Example 9

| Component | Weight (mg) |
| --- | --- |
| Lopinavir | 200 |
| Copovidone | 683.3 |
| Span40 | 67.2 |
| colloidal silica | 9.6 |
| Sodium stearylfumarate | 7.9 |
| colloidal silica | 11.3 |
| Isomalt DC100 | 129.1 |
| Sodium dodecyl sulfate | 15.6 |

Copovidone (N-vinyl pyrrolidone/vinyl acetate copolymer 60:40; 683.3 parts by weight) was blended with Span 40 (sorbitan monopalmitate; 67.2 parts by weight) in a Diosna high-shear mixer. The resulting granules were mixed with lopinavir (200 parts by weight) and colloidal silica (9.6 parts by weight). The powdery mixture was then fed into a twin-screw extruder (screw diameter 18 mm) at a rate of 2.1 kg/h and a melt temperature of 119° C. The extrudate was cut into pieces and allowed to solidify. The extruded pieces were milled using a high impact universal mill. The milled material was blended in a bin blender with sodium stearylfumarate (7.9 parts by weight), colloidal silica (11.3 parts by weight), isomalt DC100 (129.1 parts by weight) and sodium dodecyl sulfate (15.6 parts by weight). The blend was compressed and then film-coated in a coating pan by spraying an aqueous dispersion for film coating (Opadry, available from Colorcon) at a temperature of 60° C.

The bioavailability of the formulation was assessed using beagle dogs as in Example 1. Tablets corresponding to 200 mg lopinavir were coadministered to dogs together with 50 mg ritonavir. The dose-adjusted AUC of lopinavir was 38.8 µg.h/ml/100 mg.

Example 10

| Component | Weight (mg) |
|---|---|
| Ritonavir | 50 |
| Copovidone | 151.5 |
| Cremophor RH40 | 24 |
| colloidal silica | 3.8 |
| PEG 6000 | 12 |
| Isomalt DC100 | 31.9 |
| Calcium silicate | 4.2 |

Copovidone (N-vinyl pyrrolidone/vinyl acetate copolymer 60:40; 151.5 parts by weight) was blended with Cremophor RH40 (24 parts by weight) and PEG 6000 (12 parts by weight) in a Diosna high-shear mixer. The resulting granules were mixed with ritonavir (50 parts by weight) and colloidal silica (2.4 parts by weight). The powdery mixture was then fed into a twin-screw extruder and was melt-extruded. The extrudate was cut into pieces and allowed to solidify. The extruded pieces were milled using a high impact universal mill. The milled material was blended in a bin blender with colloidal silica (1.4 parts by weight), isomalt DC100 (31.9 parts by weight) and calcium silicate (4.2 parts by weight). The blend was compressed and then film-coated in a coating pan by spraying an aqueous dispersion for film coating (Opadry, available from Colorcon) at a temperature of 60° C.

Example 11

| Component | Weight % |
|---|---|
| Extrusion | |
| Ritonavir | 3.53 |
| Lopinavir | 14.11 |
| Copovidone | 57.71 |
| Polyoxyl 40 hydrogenated castor oil (Cremophor RH 40) | 8.47 |
| Colloidal silicon dioxide | 1.28 |
| Post extrusion | |
| Lactose | 5.88 |
| Crospovidone | 5.88 |
| Magnesium stearate | 0.49 |
| Colloidal silicon dioxide | 0.55 |
| Film coating | 2.12 |

The extruded material was milled, compressed with tableting excipients, and coated. The formulation consisted of lopinavir (200 mg/tablet), ritonavir (50 mg/tablet), copovidone as the carrier polymer, and polyoxyl 40 hydrogenated castor oil as the surfactant. For compression, outer phase excipients were added to the milled extrudate. The surfactant was incorporated prior to extrusion by granulation with a portion of the polymer.

Example 12

| Component | Weight % |
|---|---|
| Extrusion | |
| Ritonavir | 3.48 |
| Lopinavir | 13.91 |
| Copovidone | 58.06 |
| Polyoxyl 40 hydrogenated castor oil (Cremophor RH 40) | 1.67 |
| Sorbitan monopalmitate (Span 40) | 4.67 |
| PEG 6000 | 0.83 |
| Colloidal silicon dioxide | 0.84 |
| Post extrusion | |
| Isomalt | 11.29 |
| Calcium silicate | 1.47 |
| Sodium stearyl fumarate | 0.59 |
| Sodium lauryl sulfate | 0.88 |
| Colloidal silicon dioxide | 0.49 |
| Film coating | 1.81 |

The tablet formulation was compressed from separately extruded lopinavir and ritonavir powder mixtures. The surfactant was incorporated prior to extrusion by granulation with a portion of the polymer.

Example 13

| Component | Weight % |
|---|---|
| Extrusion | |
| Ritonavir | 4.03 |
| Lopinavir | 16.10 |
| Copovidone | 68.74 |
| Sorbitan monolaurate (Span 20) | 6.76 |
| Colloidal silicon dioxide | 0.97 |
| Post extrusion | |
| Sodium stearyl fumarate | 0.99 |
| Colloidal silicon dioxide | 0.64 |
| Film coating | 1.77 |

The formulation was prepared by milling the extrudate, mixing with tableting excipients and compressing into tablets. An aqueous, hydroxypropyl methylcellulose based film coating was applied to the compressed tablets to enhance pharmaceutical elegance. The surfactant was incorporated prior to extrusion by granulation with a portion of the polymer.

Example 14

| Component | Weight % |
|---|---|
| Extrusion | |
| Ritonavir | 3.54 |
| Lopinavir | 14.15 |
| Copovidone | 59.54 |
| Polyoxyl 40 hydrogenated castor oil (Cremophor RH 40) | 2.56 |
| Sorbitan monolaurate (span 20) | 4.26 |
| Colloidal silicon dioxide | 0.85 |
| Post extrusion | |
| Isomalt | 11.28 |
| Calcium silicate | 0.50 |
| Sodium stearyl fumarate | 0.98 |
| Colloidal silicon dioxide | 0.50 |
| Film coating | 1.84 |

The formulation was prepared by milling the extrudate, mixing with tableting excipients and compressing into tablets. An aqueous, hydroxypropyl methylcellulose based film coating was applied to the compressed tablets to enhance pharmaceutical elegance. The surfactant was incorporated prior to extrusion by granulation with a portion of the polymer.

Example 15

| Component | Weight % |
|---|---|
| Extrusion | |
| Ritonavir | 4.17 |
| Lopinavir | 16.67 |
| Copovidone | 71.17 |
| Sorbitan monolaurate (span 20) | 6.99 |
| Colloidal silicon dioxide | 1.00 |

The formulation was extruded in the shape of a tablet without the additional processing steps of milling, compression and coating. The formulation composition included ritonavir, lopinavir, copovidone, surfactant, and colloidal silicon dioxide with the two formulations differing in the type of surfactant used. The extruded tablet formulation contained sorbitan monolaurate as the surfactant that was incorporated prior to extrusion by granulation with a portion of the polymer.

Example 16

| Component | Weight % |
|---|---|
| Extrusion | |
| Ritonavir | 4.17 |
| Lopinavir | 16.67 |
| Copovidone | 70.13 |
| Polyoxyl 40 hydrogenated castor oil (Cremophor RH 40) | 3.02 |
| Sorbitan monolaurate (span 20) | 5.02 |
| Colloidal silicon dioxide | 1.00 |

The formulation was extruded in the shape of a tablet without the additional processing steps of milling, compression and coating. The formulation composition included ritonavir, lopinavir, copovidone, surfactant, and colloidal silicon dioxide with the two formulations differing in the type of surfactant used. The extruded tablet formulation contained both polyoxyl 40 hydrogenated castor oil and sorbitan monolaurate as the surfactants. The surfactants were incorporated prior to extrusion by granulation with a portion of the polymer.

This dosage form was characterized by an excellent stability and, in particular, exhibit high resistance against recrystallization or decomposition of the active ingredient(s). Thus, upon storage for 6 weeks at 40° C. and 75% humidity (e.g., when kept in high density polyethylene (HDPE) bottles without desiccant), the dosage forms according to the present invention did not exhibit any sign of crystallinity (as evidenced by DSC or WAXS analysis) and contained at least about 98% of the initial active ingredient content (as evidenced by HPLC analysis).

In vitro dissolution tests were performed on several of the formulation disclosed in the Examples above. The testing method and conditions are shown in the table below.

| | |
|---|---|
| Apparatus: | USP Apparatus 2 (paddle) |
| Agitation: | 75 rpm |
| Medium: | 0.06M POE10LE (Polyoxyethylene 10 Lauryl Ether) |
| Temperature: | 37° C. |
| Profile Times: | 15, 30, 60, 90, 120 and 150 minutes with medium replacement |
| Proposed Specification: | Q = 80% in 120 minutes |

The results are shown below. Table 1 shows the mean % lopinavir releaseded in minutes for the formulations disclosed in Examples 9-10 and 12-16.

TABLE 1

| Mean % lopinavir dissolved in minutes. | | | | | | | |
|---|---|---|---|---|---|---|---|
| Example No. | Mean % Lopinavir Dissolved (minutes) | | | | | | |
| | 15 | 30 | 45 | 60 | 90 | 120 | 150 |
| 9 | 30.4 | 56.0 | 75.1 | 88.7 | 100.6 | 101.1 | 100.9 |
| 10 | — | — | — | — | — | — | — |
| 12 | 21.6 | 47.3 | 67.1 | 82.0 | 96.0 | 100.8 | 101.1 |
| 13 | 20.6 | 43.0 | 61.3 | 75.4 | 92.2 | 98.1 | 99.2 |
| 13 | 23.1 | 47.3 | — | 80.0 | 93.9 | 98.1 | 98.8 |
| 14 | 21.0 | 47.6 | 69.9 | 85.6 | 98.5 | 101.1 | 101.7 |
| 15 | 36.9 | 63.0 | 81.7 | 93.2 | 102.0 | 103.0 | 103.1 |
| 16 | 32.1 | 57.0 | 74.9 | 86.5 | 95.9 | 99.2 | 99.6 |

Table 2 shows the mean % ritonavir dissolved in minutes for the formulations disclosed in Examples 9-10 and 12-16.

TABLE 2

| Mean % ritonavir dissolved in minutes | | | | | | | |
|---|---|---|---|---|---|---|---|
| Example No. | Mean % Ritonavir Dissolved (minutes) | | | | | | |
| | 15 | 30 | 45 | 60 | 90 | 120 | 150 |
| 9 | — | — | — | — | — | — | — |
| 10 | — | 76.5 | 91.1 | 95.0 | 96.9 | — | — |
| 12 | 21.8 | 46.4 | 65.6 | 79.8 | 93.3 | 98.1 | 98.3 |
| 13 | 19.8 | 41.6 | 59.4 | 73.4 | 90.0 | 96.2 | 97.5 |
| 13 | 23.1 | 46.0 | — | 78.0 | 92.0 | 96.3 | 96.9 |
| 14 | 21.0 | 45.4 | 66.5 | 82.3 | 95.1 | 100.1 | 98.2 |
| 15 | 34.4 | 59.1 | 76.9 | 88.0 | 96.6 | 67.6 | 97.7 |
| 16 | 30.5 | 54.4 | 71.7 | 83.1 | 92.3 | 95.4 | 96.0 |

Therefore, in one embodiment the present invention provides for example, a pharmaceutical dosage form comprising lopinavir in a therapeutically effective amount, said dosage form providing an in vitro dissolution profile wherein about 20% to about 30% of lopinavir is released from about 0 to about 15 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising lopinavir in a therapeutically effective amount, said dosage form providing an in vitro dissolution profile wherein about 20% to about 30% of lopinavir is released from about 0 to about 15 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising lopinavir in a therapeutically effective amount, said dosage form providing an in vitro dissolution profile wherein about 43% to about 63% of lopinavir is released from about 15 to about 30 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising lopinavir in a therapeutically effective amount, said dosage form providing an in vitro dissolution profile wherein about 61.3% to about 81.7% of lopinavir is released from about 30 to about 45 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising lopinavir in a therapeutically effective amount, said dosage form providing an in vitro dissolution profile wherein about 75.4% to about 93.2% of lopinavir is released from about 45 to about 60 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising ritonavir in a therapeutically effective amount, said dosage form providing an in vitro dissolution profile wherein about 19.8% to about 34.4% of ritonavir is released from about 0 to about 15 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising ritonavir in a therapeutically effective amount, said dosage form providing an in vitro dissolution profile wherein about 41.6% to about 76.5% of ritonavir is released from about 15 to about 30 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising ritonavir in a therapeutically effective amount, said dosage form providing an in vitro dissolution profile wherein about 59.4% to about 91.1% of ritonavir is released from about 30 to about 45 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising ritonavir in a therapeutically effective amount, said dosage form providing an in vitro dissolution profile wherein about 73.4% to about 95% of ritonavir is released from about 45 to about 60 minutes using a USP apparatus 2 (paddle) at 75 rpm with a 0.06M POE10LE (Polyoxyethylene 10 Lauryl Ether) medium at 37° C.

In one embodiment the present invention provides for example, a pharmaceutical dosage form comprising lopinavir in a therapeutically effective amount, said dosage form providing an in vitro dissolution profile using a USP apparatus 2 (paddle) at 75 rpm with a 0.06M POE10LE (Polyoxyethylene 10 Lauryl Ether) medium at 37° C. wherein:
about 20% to about 30% of lopinavir is released from about 0 to about 15 minutes;
about 43% to about 63% of lopinavir is released from about 15 to about 30 minutes;
about 61.3% to about 81.7% of lopinavir is released from about 30 to about 45 minutes; and
about 75.4% to about 93.2% of lopinavir is released from about 45 to about 60 minutes.

In one embodiment the present invention provides for example, a pharmaceutical dosage form comprising ritonavir in a therapeutically effective amount, said dosage form providing an in vitro dissolution profile using a USP apparatus 2 (paddle) at 75 rpm with a 0.06M POE10LE (Polyoxyethylene 10 Lauryl Ether) medium at 37° C. wherein:
about 19.8% to about 34.4% of ritonavir is released from about 0 to about 15 minutes;
about 41.6% to about 76.5% of ritonavir is released from about 15 to about 30 minutes;
about 59.4% to about 91.1% of ritonavir is released from about 30 to about 45 minutes; and
about 73.4% to about 95% of ritonavir is released from about 45 to about 60 minutes.

In one embodiment the present invention provides for example, a pharmaceutical dosage form comprising ritonavir and lopinavir in a therapeutically effective amount, said dosage form providing an in vitro dissolution profile using a USP apparatus 2 (paddle) at 75 rpm with a 0.06M POE10LE (Polyoxyethylene 10 Lauryl Ether) medium at 37° C. wherein:
about 19.8% to about 34.4% of ritonavir is released and about 20% to about 30% of lopinavir is released from about 0 to about 15 minutes;
about 41.6% to about 76.5% of ritonavir and about 43% to about 63% of lopinavir is released from about 15 to about 30 minutes;
about 59.4% to about 91.1% of ritonavir and about 61.3% to about 81.7% of lopinavir is released from about 30 to about 45 minutes; and
about 73.4% to about 95% of ritonavir and about 75.4% to about 93.2% of lopinavir is released from about 45 to about 60 minutes.

In order to understand lopinavir exposure among humans receiving the dosage form of the present invention and currently marketed Kaletra gelatin capsule, probability distributions were constructed from studies described below. It was assumed that the natural logarithms of lopinavir Cmax and AUC∞ followed normal distributions with mean (μ) and variance (σ2) for each formulation. These values were taken from single 400/100 mg lopinavir/ritonavir dose, 4 or 5 period, randomized, open-label cross-over studies in healthy human volunteers under controlled meal conditions (either fasting, moderate-fat, or high-fat). Each study had between 48 and 63 subjects with a washout between periods of at least 7 days. The mean values for lopinavir Cmax and AUC∞ under moderate-fat meal condition were obtained from the central values in a cross-study meta-analysis of bioequivalence as generally known by those having ordinary skill in the art. The variance values for the distribution were obtained from the between-subject variability estimated for the dosage form of the present invention and the currently marketed Kaletra gelatin capsule using the SAS Procedure Mixed as generally known by those having ordinary skill in the art.

The probability distributions of lopinavir Cmax and AUC∞ under fasting and high-fat meal conditions were adjusted using the point estimates from Studies C and A described below for the dosage form of the present invention and currently marketed Kaletra gelatin capsule. The variance for each of fasting and high-fat meal conditions were projected according to the magnitude of the variability relative to that of the moderate-fat meal conditions using data from studies A, B and C described below in more detail.

The probability density in relation to AUC∞ for each formulation was calculated based on the mean and variance using the following formula:

$$\frac{1}{\sqrt{2\pi}\,\sigma}\frac{e^{-(\log x-\mu)^2/(2\sigma^2)}}{AUC_\infty}$$

The probability distribution of lopinavir Cmax was constructed in the same manner.

Study A was a single-dose (lopinavir/ritonavir 400/100 mg), five-period, randomized, open-label, pivotal bioavailability study in 63 healthy subjects. The first four periods were conducted according to a complete-crossover design. Subjects were equally randomized to four sequences of Regimens A, B, C and D for Periods 1 through 4. Five subjects from each sequence group who completed Periods 1 through 4 were randomly chosen to participate in Period 5 and received Regimen E. A washout interval of at least 7 days separated the doses of the five study periods. The five regimens were:

Regimen A: Three lopinavir/ritonavir 133.3/33.3 mg currently marketed Kaletra gelatin capsules following a moderate-fat breakfast;

Regimen B: Three lopinavir/ritonavir 133.3/33.3 mg currently marketed Kaletra gelatin capsules under fasting conditions;

Regimen C: Two lopinavir/ritonavir 200/50 mg dosage forms of the present invention following a moderate-fat breakfast;

Regimen D: Two lopinavir/ritonavir 200/50 mg dosage forms of the present invention under fasting conditions; and Regimen E: Two lopinavir/ritonavir 200/50 mg dosage forms of the present invention following a high-fat breakfast.

Study B was a single-dose (lopinavir/ritonavir 400/100 mg), non-fasting, moderate-fat, open-label, four-period, randomized, complete-crossover, pivotal bioavailability study in 48 healthy subjects. Subjects were randomly assigned in equal numbers to receive one of four sequences of Regimens A, B, C and D defined as follows:

Regimen A: Two lopinavir/ritonavir 200/50 mg dosage forms of the present invention (Lot 1);

Regimen B: Two lopinavir/ritonavir 200/50 mg dosage forms of the present invention (Lot 2);

Regimen C: Two lopinavir/ritonavir 200/50 mg dosage forms of the present invention (Lot 3);

Regimen D: Three lopinavir/ritonavir 133.3/33.3 mg currently marketed Kaletra gelatin capsules.

The single doses were administered in the morning on Study Day 1 of each period following a moderate-fat breakfast. A washout interval of 7 days separated the doses of the four study periods.

Study C was a Phase 1, single-dose, fasting and non-fasting, open-label, randomized, five-period, partial crossover, single-center study in 56 healthy subjects. The currently marketed Kaletra liquid and gelatin capsule formulations were administered to provide a single dose of lopinavir/ritonavir 400/100 mg. Both formulations were given under fasting conditions and following moderate and high-fat meals.

It has been discovered that the dosage form of the present invention provides a substantially lower variation in Cmax and AUC∞ from the $5^{th}$ to the $95^{th}$ percentiles for lopinavir when administered to a subject whether fed or fasted than the gelatin capsule formulation. That is, the dosage form of the present invention provides a smaller Δ Cmax and Δ AUC∞ from the $5^{th}$ to the $95^{th}$ percentiles for lopinavir than the Kaletra gelatin capsule formulation. This is shown both graphically in FIGS. 1 and 2 as well as numerically in Tables 3-5.

The dosage form of the present invention also provides a substantially lower variation in Cmax and AUC∞ from the $25^{th}$ to the $75^{th}$ percentiles for lopinavir when administered to a subject whether fed or fasted than the gelatin capsule formulation. That is, the dosage form of the present invention provides a smaller Δ Cmax and Δ AUC∞ from the $25^{th}$ to the $75^{th}$ percentiles for lopinavir than the Kaletra gelatin capsule formulation. This is shown both graphically in FIGS. 1 and 2 as well as numerically in Tables 3-5.

TABLE 3

Lopinavir bioavailability from Kaletra ® Gelatin Capsule v. Claimed Dosage Form under Fasted Conditions.

| Dosage Form | Percentile | AUC∞ (µg · h/mL) | Cmax (µg/mL) |
|---|---|---|---|
| Gelatin Capsule | 5 | 10.6 | 1.31 |
| | 25 | 26.67 | 2.698 |
| | 50 | 52.22 | 4.946 |
| | 75 | 102.2 | 9.057 |
| | 95 | 268.5 | 21.52 |
| Solid Dosage Form | 5 | 33.15 | 3.051 |
| | 25 | 54.09 | 4.882 |
| | 50 | 76.02 | 6.809 |
| | 75 | 106.8 | 9.379 |
| | 95 | 174.3 | 15.03 |

TABLE 4

Lopinavir bioavailability from Kaletra ® Gelatin Capsule v. Claimed Dosage Form under Moderate-Fat Meal Conditions.

| Dosage Form | Percentile | AUC∞ (µg · h/mL) | Cmax (µg/mL) |
|---|---|---|---|
| Gelatin Capsule | 5 | 28.43 | 2.615 |
| | 25 | 52.9 | 4.433 |
| | 50 | 81.45 | 6.424 |
| | 75 | 125.41 | 9.314 |
| | 95 | 233.5 | 16.316 |
| Solid Dosage Form | 5 | 46.06 | 3.829 |
| | 25 | 71.27 | 5.91 |
| | 50 | 96.54 | 8.004 |
| | 75 | 130.8 | 10.89 |
| | 95 | 202.3 | 16.77 |

TABLE 5

Lopinavir bioavailability from Kaletra ® Gelatin Capsule v. Claimed Dosage Form under High-Fat Meal Conditions.

| Dosage Form | Percentile | AUC∞ (µg · h/mL) | Cmax (µg/mL) |
|---|---|---|---|
| Gelatin Capsule | 5 | 37.56 | 2.865 |
| | 25 | 68.05 | 4.882 |
| | 50 | 102.9 | 7.066 |
| | 75 | 155.5 | 10.28 |
| | 95 | 287.7 | 17.47 |
| Solid Dosage Form | 5 | 57.77 | 3.302 |
| | 25 | 75.26 | 5.011 |
| | 50 | 90.46 | 6.713 |
| | 75 | 108.7 | 8.993 |
| | 95 | 141.67 | 13.683 |

For example, it is shown in Table 3 that the Kaletra gelatin capsule formulation provides a Δ AUC∞ of 257.9 µg•h/mL from the $5^{th}$ to the $95^{th}$ percentile, and Δ Cmax of 20.21 µg/mL from the $5^{th}$ to the $95^{th}$ percentile. In contrast, the dosage form of the present invention provides a Δ AUC∞ of 141.15 μg•h/mL from the 5$^{th}$ to the 95$^{th}$ percentile, and Δ Cmax of 11.98 μg/mL from the 5$^{th}$ to the 95$^{th}$ percentile.

In other words, 90% of the study subjects in Table 3 will have a Δ AUC∞ of 257.9 μg•h/mL and Δ Cmax of 20.21 μg/mL upon dosing of the Kaletra gelatin capsule formulation, while 90% of the study subjects will have a Δ AUC∞ of 141.15 μg•h/mL and Δ Cmax of 11.98 μg/mL upon dosing of dosage form of the present invention.

Again, looking at Table 3, this difference is even evident at the 25$^{th}$ to the 75$^{th}$ percentile wherein the Kaletra gelatin capsule formulation provides a Δ AUC∞ of 75.53 μg•h/mL and Δ Cmax of 6.36 μg/mL for 50% of the study subjects. In stark contrast, the dosage form of the present invention provides a Δ AUC∞ of 52.71 μg•h/mL and Δ Cmax of 4.5 μg/mL for 50% of the study subjects.

The dosage form of the present invention demonstrates no food effect. The ratio "X" of AUC∞ fed to AUC∞ fasted for lopinavir is calculated using the formula below, $$\frac{AUC_\infty(\text{fed})}{AUC_\infty(\text{fasted})} = X.$$

The calculation is performed for each individual member of a study population in a given trial. The mean value is calculated by adding up the "X" values of every subject and then dividing the total by the number of subjects in the trial. When the "X" value is in the range of about 0.7 to about 1.43, it is determined that the dosage form has no food effect. That is, the dosage form will have substantially the same bioavailability whether it is administered on a full or empty stomach.

The ratio "Y" of Cmax fed to Cmax fasted for lopinavir is calculated using the formula below, $$\frac{C\text{max(fed)}}{C\text{max(fasted)}} = X.$$

The calculation is performed for each individual member of a study population in a given trial. The mean value is calculated by adding up the "Y" values of every subject and then dividing the total by the number of subjects in the trial. When the "Y" value is in the range of about 0.7 to about 1.43, it is determined that the dosage form has no food effect. That is, the dosage form will have substantially the same bioavailability whether it is administered on a full or empty stomach.

Table 6 below better illustrates how "X" and "Y" values are calculated from individual members of a study population totaling 20 subjects.

TABLE 6

Fed/Fasted Ratio of Cmax and AUC for individual subjects.

| Subject | Cmax (fed)/Cmax (fasted) | AUC∞ (fed)/ AUC∞ (fasted) |
|---|---|---|
| 1 | 1.10 | 0.93 |
| 2 | 0.86 | 0.86 |
| 3 | 0.74 | 1.25 |
| 4 | 1.69 | 2.70 |
| 5 | 0.89 | 1.07 |
| 6 | 1.36 | 1.25 |
| 7 | 0.97 | 1.25 |
| 8 | 0.77 | 1.05 |
| 9 | 1.30 | 1.77 |
| 10 | 1.48 | 2.23 |

TABLE 6-continued

Fed/Fasted Ratio of Cmax and AUC for individual subjects.

| Subject | Cmax (fed)/Cmax (fasted) | AUC∞ (fed)/ AUC∞ (fasted) |
|---|---|---|
| 11 | 1.12 | 1.45 |
| 12 | 0.60 | 0.67 |
| 13 | 0.94 | 0.75 |
| 14 | 1.48 | 1.82 |
| 15 | 1.19 | 1.32 |
| 16 | 0.94 | 0.93 |
| 17 | 0.41 | 0.62 |
| 18 | 0.98 | 1.49 |
| 19 | 0.95 | 1.01 |
| 20 | 1.05 | 1.13 |
| Total number of subjects (N) | 20 | 20 |
| Total value | 20.82 | 25.55 |
| Mean value | (20.82/20) = 1.04 | (25.55/20) = 1.28 |

Table 6. shows the mean Cmax value is 1.04 and the mean AUC∞ value is 1.28. These values are both individually within the range of about 0.7 to about 1.43 and show that the dosage form of the present invention has no food effect.

In conducting several studies comparing the dosage form of the present invention to the currently marketed Kaletra gelatin capsule formulation it has also been found that the dosage form of the present invention minimizes or eliminates many adverse events. Particularly, it has been found that the dosage form of the present invention minimizes or eliminates gastrointestinal adverse events. Table 7. below compares the number and types of adverse events in terms of percentage of study populations when administered the dosage form of the present invention versus the currently marketed Kaletra gelatin capsule formulation

TABLE 7

Percentage of study population suffering adverse event by type.

| Type of adverse event | Presently claimed dosage form (% of study subjects) | Currently marketed Kaletra gelatin cvapsule formulation (% of study subjects) |
|---|---|---|
| Abdominal pain | 13 | 20 |
| Asthenia | 0 | 23 |
| Headache | 13 | 23 |
| Diarrhea | 17 | 50 |
| Flatulence | 4 | 14 |
| Nausea | 9 | 23 |
| Taste Perversion | 4 | 11 |

What is claimed is:

1. A method of treating HIV, comprising administering, to a patient in need thereof a solid pharmaceutical dosage form, wherein said dosage form is taken by said patient without food or under a fasting condition, and wherein said dosage form comprises a solid solution or solid dispersion of lopinavir and ritonavir in a matrix, said matrix comprising at least one pharmaceutically acceptable water-soluble polymer and at least one pharmaceutically acceptable surfactant, wherein said surfactant is sorbitan monolaurate, and said water-soluble polymer has a Tg of at least 50° C.

2. The method of claim 1, wherein each of said at least one pharmaceutically acceptable water-soluble polymer has a Tg of at least 50° C.

3. The method of claim 2, wherein said at least one pharmaceutically acceptable water-soluble polymer comprises a copolymer of N-vinyl pyrrolidone and vinyl acetate.

4. The method of claim 2, wherein said at least one pharmaceutically acceptable water-soluble polymer comprises copovidone.

5. The method of claim 1, wherein said dosage form comprises a solid solution of lopinavir and ritonavir in said matrix.

6. The method of claim 5, wherein each of said at least one pharmaceutically acceptable water-soluble polymer has a Tg of at least 50° C. and each of said at least one pharmaceutically acceptable surfactant has an HLB value of from 4 to 10.

7. The method of claim 6, wherein said at least one pharmaceutically acceptable surfactant accounts for at least 50% by weight of the total amount of surfactants comprised in said dosage form.

8. The method of claim 6, wherein said dosage form comprises from 50 to 85% by weight of the dosage form of said at least one pharmaceutically acceptable water-soluble polymer, and from 2 to 20% by weight of the dosage form of said at least one pharmaceutically acceptable surfactant.

9. The method of claim 8, wherein said at least one pharmaceutically acceptable water-soluble polymer comprises a copolymer of N-vinyl pyrrolidone and vinyl acetate.

10. The method of claim 8, wherein said at least one pharmaceutically acceptable water-soluble polymer is copovidone.

11. A method of treating HIV, comprising administering to a patient in need thereof a solid pharmaceutical dosage form, wherein said dosage form is taken by said patient without food or under a fasting condition, and said dosage form comprises a solid solution or solid dispersion of lopinavir and ritonavir in a matrix, said matrix comprising sorbitan monolaurate and a pharmaceutically acceptable water-soluble polymer having a Tg of at least 50° C., and wherein when said dosage form is dissolved in vitro using a USP apparatus 2 (paddle) at 75 rpm with a 0.06M POEIOLE (Polyoxyethylene 10 Lauryl Ether) medium at 37° C., 20% to 30% of lopinavir in said dosage form is released from 0 to 15 minutes, or 43% to 63 % of lopinavir in said dosage form is released from 15 to 30 minutes, or 61.3% to 81.7% of lopinavir in said dosage form is released from 30 to 45 minutes, or 75.4% to 93.2% of lopinavir in said dosage form is released from 45 to 60 minutes, and wherein when said dosage form is dissolved in vitro using a USP apparatus 2 (paddle) at 75 rpm with a 0.06M POE10LE (Polyoxyethylene 10 Lauryl Ether) medium at 37° C., from 19.8% to 34.4% of ritonavir in said dosage form is released from 0 to 15 minutes, or from 41.6% to 76.5% of ritonavir in said dosage form is released from 15 to 30 minutes, or from 59.4% to 91.1% of ritonavir in said dosage form is released from 30 to 45 minutes, or from 73.4% to 95% of ritonavir in said dosage form is released from 45 to 60 minutes.

12. A method of treating HIV, comprising administering to a patient in need thereof a solid pharmaceutical dosage form, wherein said dosage form is taken by said patient without food or under a fasting condition, and said dosage form comprises a solid solution or solid dispersion of lopinavir and ritonavir in a matrix, said matrix comprising sorbitan monolaurate and a pharmaceutically acceptable water-soluble polymer having a Tg of at least 50° C., and wherein upon administration of said dosage form to each member of a study population, the mean of lopinavir AUC∞ (fed) over lopinavir AUC∞ (fasted) ratios for all members of the study population is from 0.7 to 1.43.

13. A method of treating HIV, comprising administering to a patient in need thereof a solid pharmaceutical dosage form, wherein said dosage form is taken by said patient without food or under a fasting condition, and said dosage form comprises a solid solution or solid dispersion of lopinavir and ritonavir in a matrix, said matrix comprising sorbitan monolaurate and a pharmaceutically acceptable water-soluble polymer having a Tg of at least 50° C., and wherein upon administration of said dosage form to each member of a study population, the mean of lopinavir Cmax (fed) over lopinavir Cmax (fasted) ratios for all members of the study population is from 0.7 to 1.43.

14. A method of treating an HIV patient, comprising administering to said patient a solid pharmaceutical dosage form, wherein said dosage form is taken by said patient without food, wherein said dosage form comprises at least one HIV protease inhibitor formulated in solid solution, said solid solution comprising at least one pharmaceutically acceptable water-soluble polymer having a Tg of at least 50° C. and sorbitan monolaurate, and wherein said at least one HIV protease inhibitor comprises lopinavir and ritonavir.

15. The method of claim 14, wherein each of said at least one pharmaceutically acceptable water-soluble polymer has a Tg of at least 50° C..

16. The method of claim 15, wherein said at least one pharmaceutically acceptable water-soluble polymer comprises a copolymer of N-vinyl pyrrolidone and vinyl acetate.

17. The method of claim 15, wherein said dosage form comprises from 50 to 85% by weight of the dosage form of said at least one pharmaceutically acceptable water-soluble polymer, and from 2 to 20% by weight of the dosage form of said sorbitan monolaurate.

18. The method of claim 17, wherein said at least one pharmaceutically acceptable water-soluble polymer is copovidone.

19. A method of treating an HIV patient, comprising administering to said patient a solid pharmaceutical dosage form, wherein said dosage form is taken by said patient without food, wherein said dosage form comprises ritonavir and lopinavir formulated in solid solution or solid dispersion, said solid solution or solid dispersion comprising a pharmaceutically acceptable water-soluble polymer having a Tg of at least 50° C. and sorbitan monolaurate.

20. The method of claim 19, wherein said water-soluble polymer is copolymer of N-vinyl pyrrolidone and vinyl acetate.

21. A method of claim 20, wherein said ritonavir and lopinavir are present in an amount from 5% to 30% by weight of the dosage form, said copolymer of N-vinyl pyrrolidone and vinyl acetate is present from 50% to 85% by weight of the dosage form, and said sorbitan monolaurate is present from 2% to 20% by weight of the dosage form.

22. The method of claim 19, wherein said water-soluble polymer is copovidone.

23. The method of claim 22, wherein said solid solution or solid dispersion comprises 4.17 weight % ritonavir, 16.67 weight % lopinavir, 71.16 weight % copovidone, and 7.0 weight % sorbitan monolaurate.

24. The method of claim 22, wherein said solid solution or solid dispersion is a solid solution.

25. The method of claim 19, wherein said solution or solid dispersion is solid solution.

26. The method of claim 21, wherein said solution or solid dispersion is solid solution.

27. The method of claim 26, wherein said water soluble polymer is copovidone.

28. The method of claim 23, wherein said solution or solid dispersion is solid solution.

29. A method of treating an HIV patient, comprising administering to said patient a solid pharmaceutical dosage form, wherein said dosage form is taken by said patient without food, wherein said dosage form comprises ritonavir and lopinavir formulated in solid solution or solid dispersion, said solid solution or solid dispersion comprising a pharmaceutically acceptable water-soluble polymer having a Tg of at least 50° C. and sorbitan monopalmitate.

30. The method of claim 29, wherein said water-soluble polymer is copolymer of N-vinyl pyrrolidone and vinyl acetate.

31. A method of claim 30, wherein said ritonavir and lopinavir are present in an amount from 5% to 30% by weight of the dosage form, said copolymer of N-vinyl pyrrolidone and vinyl acetate is present from 50% to 85% by weight of the dosage form, and said sorbitan monopalmitate is present from 2% to 20% by weight of the dosage form.

32. The method of claim 31, wherein said water-soluble polymer is copovidone.

33. The method of claim 29, wherein said solid solution or solid dispersion is solid solution.

34. The method of claim 31, wherein said solid solution or solid dispersion is solid solution.

35. The method of claim 32, wherein said solution or solid dispersion is solid solution.

* * * * *

UNITED STATES PATENT AND TRADEMARK OFFICE
CERTIFICATE OF CORRECTION

| | | |
|---|---|---|
| PATENT NO. | : 8,377,952 B2 | Page 1 of 1 |
| APPLICATION NO. | : 11/064467 | |
| DATED | : February 19, 2013 | |
| INVENTOR(S) | : Rosenberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1335 days.

Signed and Sealed this
Second Day of June, 2015

Michelle K. Lee
*Director of the United States Patent and Trademark Office*